United States Patent
Zhang et al.

(10) Patent No.: US 11,306,112 B2
(45) Date of Patent: Apr. 19, 2022

(54) BIPHENYL TETRADENTATE PHOSPHITE COMPOUND: PREPARATION METHOD AND APPLICATION THEREOF

(71) Applicant: HUIZHOU CATALYS TECHNOLOGY CO., LTD, Huizhou (CN)

(72) Inventors: Runtong Zhang, Shenzhen (CN); Xin Yan, Shenzhen (CN); Jianghua Peng, Shenzhen (CN); Jianxin Wang, Shenzhen (CN); Xintong He, Shenzhen (CN)

(73) Assignee: GUANGDONG OXO CHEM LTD., Huizhou (CN)

( * ) Notice: Subject to any disclaimer, the term of this patent is extended or adjusted under 35 U.S.C. 154(b) by 0 days.

(21) Appl. No.: 17/172,021

(22) Filed: Feb. 9, 2021

(65) Prior Publication Data

US 2021/0261586 A1    Aug. 26, 2021

(30) Foreign Application Priority Data

Feb. 10, 2020 (CN) .......................... 202010084223.6
Aug. 10, 2020 (CN) .......................... 202010794422.6
Oct. 30, 2020 (CN) .......................... 202011192970.8

(51) Int. Cl.
*C07F 9/00* (2006.01)
*C07C 45/50* (2006.01)
*C07C 37/60* (2006.01)
*C07F 9/6574* (2006.01)
*B01J 31/22* (2006.01)

(52) U.S. Cl.
CPC ....... *C07F 9/65746* (2013.01); *B01J 31/2213* (2013.01); *C07C 37/60* (2013.01); *C07C 45/505* (2013.01); *B01J 2231/321* (2013.01); *B01J 2531/822* (2013.01)

(58) Field of Classification Search
CPC ... C07F 9/65746; C07C 37/60; C07C 45/505; B01J 31/2213
See application file for complete search history.

(56) References Cited

U.S. PATENT DOCUMENTS

| 5,840,647 | A  | * | 11/1998 | Puckette  | B01J 31/1845 502/213 |
| 7,012,162 | B2 | * | 3/2006  | Mackewitz | B01J 31/20 502/162 |
| 8,471,048 | B2 | * | 6/2013  | Kuriyama  | C07B 53/00 556/8 |
| 9,687,837 | B1 | * | 6/2017  | Devon     | C07F 9/5027 |
| 10,766,833 | B2 | * | 9/2020 | Zhang     | C07F 15/008 |

* cited by examiner

*Primary Examiner* — Sikarl A Witherspoon

(57) ABSTRACT

The disclosure relates to chemical synthesis, and more particularly to a biphenyltetradentate phosphite compound and a preparation and application thereof. The compound has a structure of formula(I):

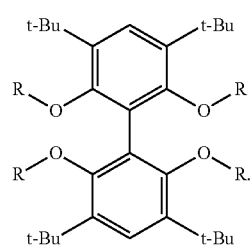

20 Claims, 3 Drawing Sheets

BIPHENYL TETRADENTATE PHOSPHITE COMPOUND: PREPARATION METHOD AND APPLICATION THEREOF

CROSS-REFERENCE TO RELATED APPLICATIONS

This application claims the benefit of priority from Chinese Patent Application Nos. 202010084223.6, 202010794422.6 and 202011192970.8, filed on Feb. 10, 2020, Aug. 10, 2020 and Oct. 30, 2020, respectively. The content of the aforementioned applications, including any intervening amendments thereto, is incorporated herein by reference in their entirety.

TECHNICAL FIELD

This application relates to chemical synthesis, and more particularly to a biphenyl tetradentate phosphite compound and a preparation and an application thereof.

BACKGROUND

Hydroformylation reaction has been widely used in industry since 1938. Considering the easy conversion into corresponding compounds, such as alcohols, carboxylic acids, esters and imines, which play an important role in the organic synthesis, the aldehydes have been produced in large scale through the hydroformylation reaction. Currently, the industrial production of the aldehydes synthesized by the hydroformylation reaction has reached 10 million tons per year. Therefore, it is of great significance to develop a high-efficiency and new tetradentate phosphite ligand and a preparation thereof the synthesis of aldehydes via hydroformylation reaction.

In the industry, phosphite esters are mainly used as antioxidants, heat stabilizers and flame retardants in the preparation of polymer materials such as plastics and rubber. In terms of the number of hydroxyl groups in the molecular structure, the phosphite esters can be divided into phosphite monoester (ROP(OH)$_2$), phosphite diester ((RO)$_2$POH) and phosphite triester ((RO)$_3$P). The phosphite ester can be further converted into a halogenatedphosphite ester after the hydroxy or alkoxy group is substituted with a halogen atom, in which chlorophosphite is considered as the most important trivalent organophosphorus intermediate. The industrial preparation of a phosphite ester generally adopts a direct esterification method, in which a halogenated trivalent phosphorus compound is used as a raw material and reacted with alcohols under a certain reaction condition.

Propylene is used as a raw material to prepare butyraldehyde by the hydroformylation reaction. The butyraldehyde then undergoes aldol condensation and hydrogenation to form dioctyl phthalate (DEHP), which is widely used as a plasticizer in the industry. The annual production of the DEHP has exceeded 3 million tons in China, and the annual production of the DEHP is as high as 10 million tons in the world. However, the price of the propylene has increased year by year. In addition, the plasticizer DEHP is prone to decomposition and volatilization due to its small molecular weight and is toxic to the human body, and thus the production and recycling of DEHP have been prohibited in 2015 according to the EU REACH regulations. Currently, a novel plasticizer bis(2-propylheptyl) phthalate (DPHP) with a high molecular weight is designed, which is prepared from valeraldehyde formed by hydroformylation of etherified C4 or etherified butene (i.e. C4 residues from MTBE process) or mixed butene (from Naphtha cracking or MTO process). The DPHP is not prone to decomposition and has low toxicity. At present, the improved process is expected to gradually replace traditional technology. The traditional technology based on triphenylphosphine (PPh$_3$) can only realize the hydroformylation of 1-butene. Compared to the 1-butene, the mixed butene/the post-MTEB butene has relative lower cost. Currently, the hydroformylation is performed mainly based on PPh$_3$ or a bidentate phosphite ligands (Biphephos) prepared by Dow Chemical Company. However, it is required to pay licensing fee and transfer fee when using the foreign catalysts and processes. In addition, the Biphephos of the Dow Chemical fails to maintain a relatively high stability for a long time in the air and is prone to undergoing hydrolysis and acidolysis. Moreover, it is easy to cause a blockage in the pipeline, and it is also needed to add the ligand to ensure the catalytic activity during the process.

SUMMARY

An object of this application is to provide a biphenyl tetradentate phosphite compound to overcome the above technical problems.

Technical solutions of the present disclosure are described as follows.

In a first aspect, this application provides a biphenyl tetradentate phosphite compound of formula (I):

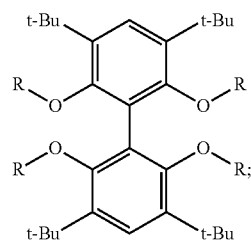

wherein R is selected from the group consisting of:

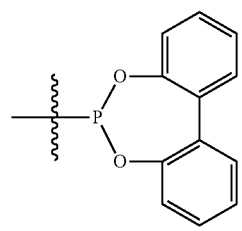

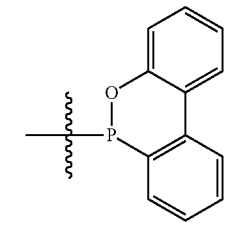

-continued
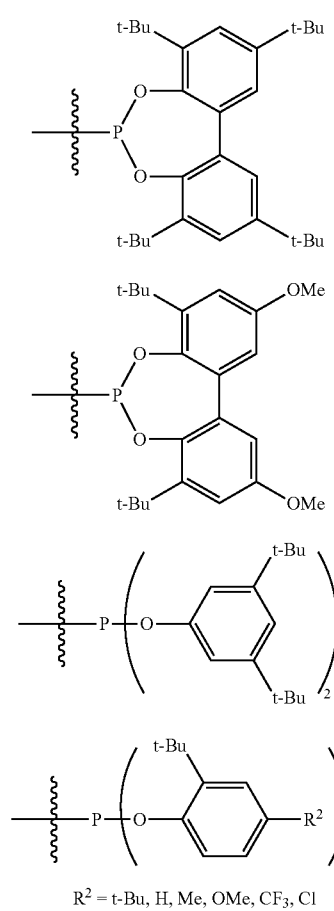
L3
L4
L5
L6
L7
L8
L9
-continued
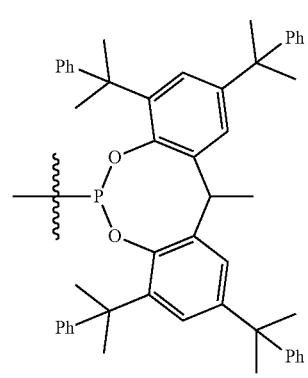
L10
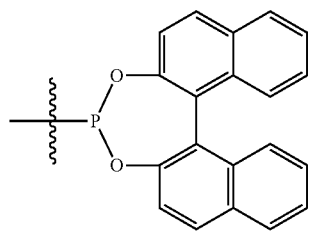
L11
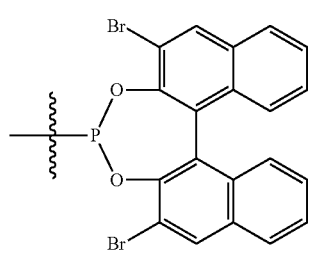
L12
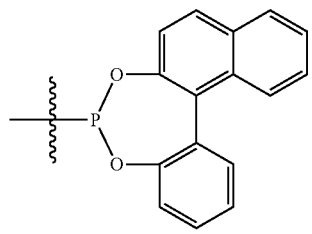
L13
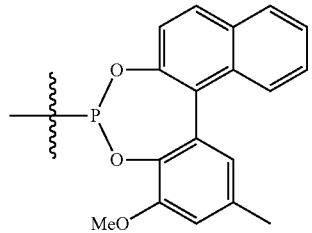
L14
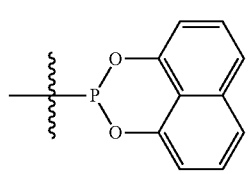
L15

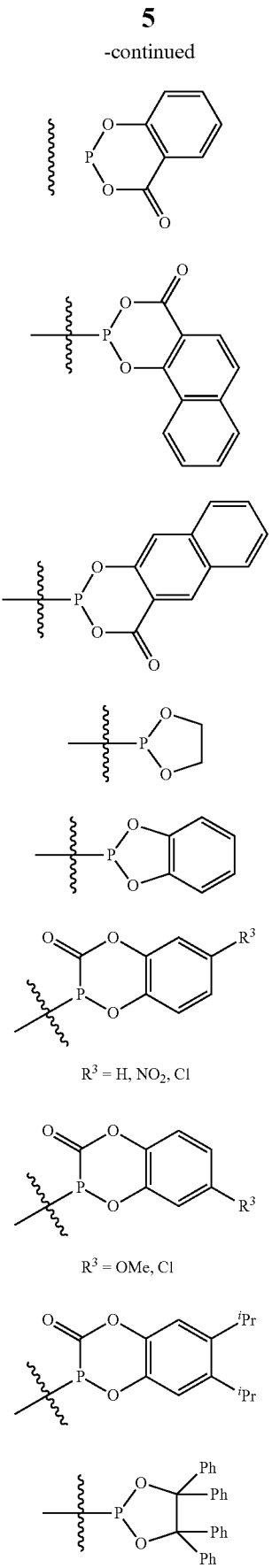

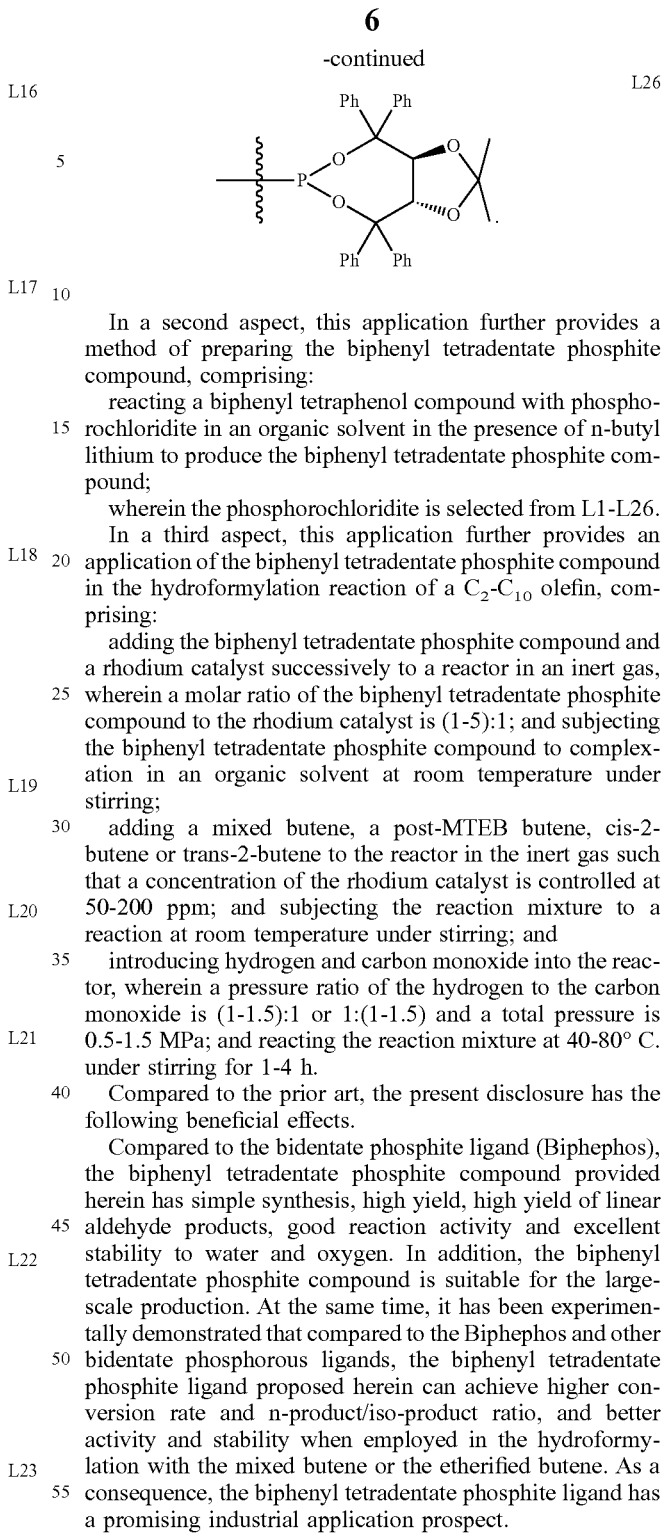

In a second aspect, this application further provides a method of preparing the biphenyl tetradentate phosphite compound, comprising:

reacting a biphenyl tetraphenol compound with phosphorochloridite in an organic solvent in the presence of n-butyl lithium to produce the biphenyl tetradentate phosphite compound;

wherein the phosphorochloridite is selected from L1-L26.

In a third aspect, this application further provides an application of the biphenyl tetradentate phosphite compound in the hydroformylation reaction of a $C_2$-$C_{10}$ olefin, comprising:

adding the biphenyl tetradentate phosphite compound and a rhodium catalyst successively to a reactor in an inert gas, wherein a molar ratio of the biphenyl tetradentate phosphite compound to the rhodium catalyst is (1-5):1; and subjecting the biphenyl tetradentate phosphite compound to complexation in an organic solvent at room temperature under stirring;

adding a mixed butene, a post-MTEB butene, cis-2-butene or trans-2-butene to the reactor in the inert gas such that a concentration of the rhodium catalyst is controlled at 50-200 ppm; and subjecting the reaction mixture to a reaction at room temperature under stirring; and introducing hydrogen and carbon monoxide into the reactor, wherein a pressure ratio of the hydrogen to the carbon monoxide is (1-1.5):1 or 1:(1-1.5) and a total pressure is 0.5-1.5 MPa; and reacting the reaction mixture at 40-80° C. under stirring for 1-4 h.

Compared to the prior art, the present disclosure has the following beneficial effects.

Compared to the bidentate phosphite ligand (Biphephos), the biphenyl tetradentate phosphite compound provided herein has simple synthesis, high yield, high yield of linear aldehyde products, good reaction activity and excellent stability to water and oxygen. In addition, the biphenyl tetradentate phosphite compound is suitable for the large-scale production. At the same time, it has been experimentally demonstrated that compared to the Biphephos and other bidentate phosphorous ligands, the biphenyl tetradentate phosphite ligand proposed herein can achieve higher conversion rate and n-product/iso-product ratio, and better activity and stability when employed in the hydroformylation with the mixed butene or the etherified butene. As a consequence, the biphenyl tetradentate phosphite ligand has a promising industrial application prospect.

DETAILED DESCRIPTION OF EMBODIMENTS

Figure 1:
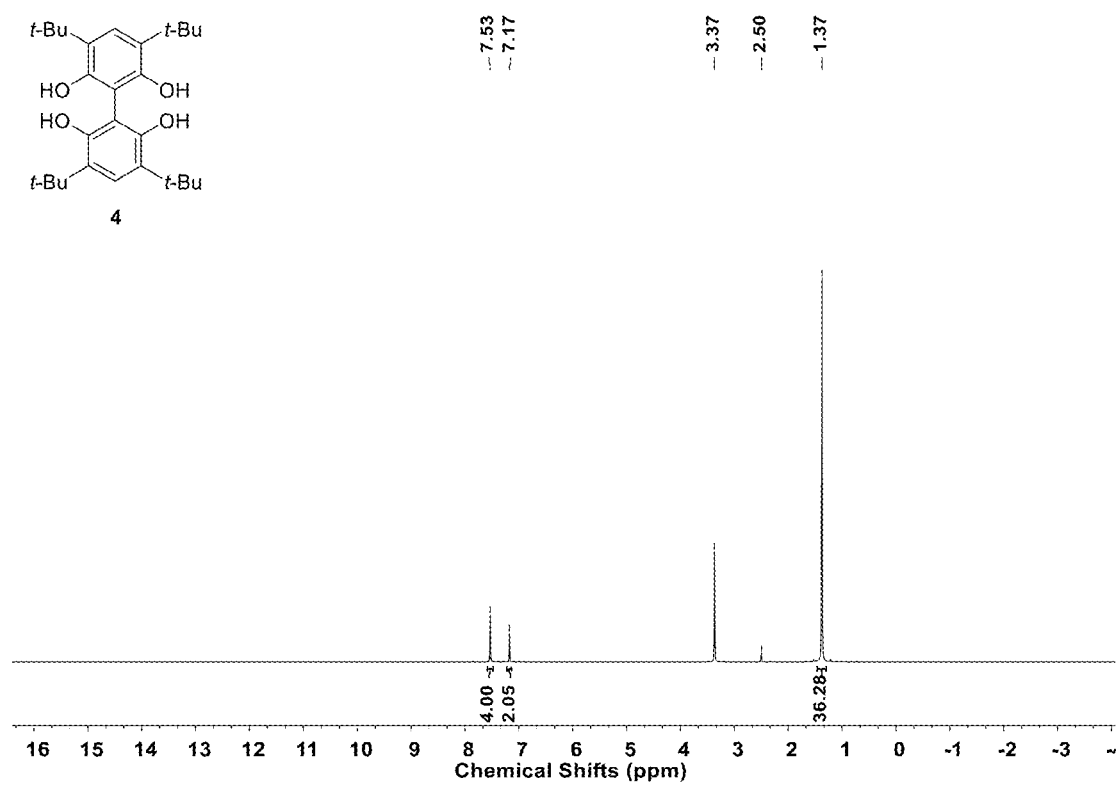
FIG. 1 is a hydrogen-nuclear magnetic resonance (H NMR) spectrum of 2,2',6,6'-tetramethoxy-3,3',5,5'-tetra-tert-butyl-1,1'-biphenyl according to an embodiment of the present disclosure.

The present disclosure will be further described in detail with reference to the embodiments and the accompanying drawings to make objects, technical solutions and advantages of the present disclosure clearer. It should be understood that these embodiments are merely illustrative of the disclosure, and are not intended to limit the scope of the present disclosure.

A biphenyl tetradentate phosphite compound is provided, which has a structure of formula(I):

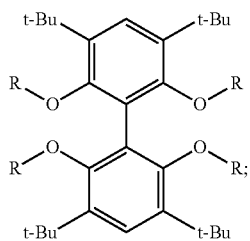

where R is a cyclic phosphite structure, preferably selected from L1-L26.

The present disclosure further provides a method of preparing the biphenyl tetradentate phosphite compound. A biphenyl tetraphenol compound is reacted with phosphorochloridite in an organic solvent in the presence of n-butyl lithium to produce the biphenyl tetradentate phosphite compound. The biphenyl tetradentate phosphine ligand is selected from L1-L26.

In an embodiment, the biphenyl tetradentate phosphite compound is 2,2',6,6'-tetra[(1,1'-biphenyl-2,2'-diyl)phosphite]-3,3',5,5'-tetra-tert-butyl-1,1'-biphenyl, which is prepared through the following steps.

(101) A biphenyl tetraphenol compound and an organic solvent are successively added to a reactor under a nitrogen atmosphere, to which n-butyl lithium is added dropwise at a low temperature. Then the reaction mixture is reacted at room temperature under reflux.

(102) A solution of a phosphorochloridite in the organic solvent is added dropwise at a low temperature. Then the reaction mixture is reacted at room temperature and concentrated to obtain the 2,2',6,6'-tetra[(1,1'-biphenyl-2,2'-diyl)phosphite]-3,3',5,5'-tetra-tert-butyl-1,1'-biphenyl.

The above-mentioned organic solvent is selected from the group consisting of tetrahydrofuran, diethyl ether, 2-methyltetrahydrofuran, dioxane and a combination thereof.

In an embodiment, the biphenyl tetraphenol compound is shown as follows:

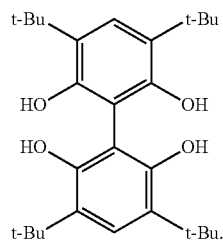 [SMILES: CC(C)(C)c1cc(C(C)(C)C)c(O)c(-c2c(O)c(C(C)(C)C)cc(C(C)(C)C)c2O)c1O]

In an embodiment, the biphenyl tetraphenol compound (2,2',6,6'-tetrahydroxy-3,3',5,5'-tetra-tert-butyl-1,1'-biphenyl) is prepared by a reaction of 4,6-di(tert-butyl)benzene-1,3-diol under the action of a metallic oxidant, an acid and a reaction solvent.

Specifically, the 2,2',6,6'-tetrahydroxy-3,3',5,5'-tetra-tert-butyl-1,1'-biphenyl is prepared through the following steps:
dissolving the 4,6-di(tert-butyl)benzene-1,3-diol in the acid in a reacting kettle, dropwise adding the metallic oxidant and the reaction solvent; and reacting the reaction mixture at −20-50° C. for 1-12 h followed by filtration to obtain the 2,2',6,6'-tetrahydroxy-3,3',5,5'-tetra-tert-butyl-1,1'-biphenyl, where a molar ratio of the metallic oxidant to the 4,6-di(tert-butyl)benzene-1,3-diol is (0.1-1.5):1.

In an embodiment, the acid is selected from the group consisting of concentrated sulfuric acid, concentrated hydrochloric acid, concentrated nitric acid, phosphonic acid, hexafluorophosphoric acid, hypochlorous acid, chlorous acid, formic acid, glacial acetic acid, peroxyacetic acid, 3-chloroperoxybenzoic acid, acetic anhydride, propionic acid, butyric acid, valeric acid, caproic acid, octanoic acid, capric acid, adipic acid, oxalic acid, malonic acid, succinic acid and a combination thereof.

In an embodiment, the metallic oxidant is selected from the group consisting of cuprous chloride, copper chloride, cuprous iodide, copper iodide, cuprous bromide, cupric bromide, copper sulfate, cupric nitrate, copper trifluoromethane sulfonate, ferrous chloride, ferric trichloride, nickel oxide, nickel dioxide, manganese trioxide, active manganese dioxide, potassium permanganate, cobalt(III) fluoride, cobaltic oxide, chromium trioxide, chromium dioxide, dichromium(III) trioxide, chromic acid, potassium dichromate, sodium dichromate, magnesium oxide, sodium iodate, sodium periodate, sodium hypochlorite, sodium chlorite, sodium chlorate, sodium perchlorate, potassium iodate, potassium periodate, potassium hypochlorite, potassium chlorite, potassium chlorate, potassium perchlorate, potassium persulfate, potassium hydrogen persulfate and a combination thereof.

In an embodiment, the biphenyl tetraphenol compound is prepared by a reaction of the 4,6-di(tert-butyl)benzene-1,3-diol under the action of a metal complex, a basic compound, an oxygen source and a reaction solvent.

Specifically, the preparation method of the biphenyl tetraphenol compound includes the steps of:
adding the reaction solvent, the basic compound and the metal complex sequentially to a reacting kettle; reacting the reaction mixture at room temperature under stirring in the presence of the oxygen source to prepare a metal-organic base complex; dropwise adding the 4,6-di(tert-butyl)benzene-1,3-diol to the reacting kettle, where the oxygen source is continuously introduced; and reacting the reaction mixture at −20-50° C. for 24-28 h followed by filtration to obtain the biphenyl tetraphenol compound; where a molar ratio of the metal complex to the 4,6-di(tert-butyl)benzene-1,3-diol is (0.005-0.1):1.

In an embodiment, the reaction solvent is selected from the group consisting of water, methanol, ethanol, isopropanol, n-butanol, tert-butanol, dichloromethane, dichloroethane, trichloromethane, benzene, toluene, xylene, 1,2-dichlorobenzene, ethyl acetate, dioxane, tetrahydrofuran, acetone, glacial acetic acid, N-methylpyrrolidone, N,N-dimethylformamide, N,N-dimethylacetamide and a combination thereof.

In an embodiment, the oxygen source is selected from the group consisting of oxygen, air, ozone, diacetoxyiodobenzene, hydrogen peroxide, tert-butyl hydroperoxide, dibenzoyl peroxide, cyclohexanone peroxide, p-benzoquinone, dichlorodicyanobenzoquinone and a combination thereof.

In an embodiment, the metal complex is selected from the group consisting of CuOAc, $Cu(OAc)_2$, $Cu(OTf)_2$, $[Cu(NH_3)_4]SO_4$, $[Cu(NH_3)_4](OH)_2$, CuCl(OH)TMEDA, Cu(TMEDA)Cl, $Cu(TMEDA)Cl_2$, $Cu(Et_3N)Cl_2$, $Cu(DTEDA)Cl_2$, $Cu(morpholine)_2Cl_2$, $Cu(PDA)_2Cl_2$, $Cu_2(TEEDA)_2Br_2$, $[Cu(MeCN)_4][PF_6]$, $Cu(PPh_3)_2Cl_2$, $K_3[Fe(CN)_6]$, $K_4[Fe(CN)_6]$, $K_3[Fe(NCS)_6]$, $Na_3[Fe(CN)_6]$, $Na_4[Fe(CN)_6]$, $Na_3[Fe(NCS)_6]$, $Fe(PPh_3)Cl$, $Ni(acac)_2$, $Ni(OAc)_2$, $Ni(CO)_4$, $Mn(acac)_2$, $Mn(OAc)_2$, $Co(acac)_2$, $Co(acac)_3$, $[Co(NH_3)_3]Cl_3$, $[Co(NH_3)_6]Cl_3$, $[Co(NO_2)_3(NH_3)]$, $Co(OAc)_2$, $CrCl_3.6H_2O$, $[Cr(H_2O)_6]Cl$, $[CrCl(H_2O)_5]Cl_2$, $CrCl_2(H_2O)_4Cl$, $[CrCl_2(H_2O)_4]Cl_2H_2O$, pyridinium chlorochromate, pyridinium dichromate, $[Mg(ClO_4)_2].6H_2O$ and a combination thereof.

In an embodiment, the basic compound is selected from the group consisting of methylamine, ethylamine, dimethylamine, diethylamine, trimethylamine, triethylamine, N,N'-dimethylaniline, N-methylaniline, aniline, diphenylamine, ethylenediamine, N-methylethylenediamine, N,N-dimethylethylenediamine, N,N'-dimethylethylenediamine, N,N,N'-trimethylethylenediamine, N,N,N',N'-tetramethylethylenediamine, N-ethylethylenediamine, N,N'-diethylethylenediamine, N,N-diethylethylenediamine, N,N,N'-triethylethylenediamine, N,N,N',N'-tetradiethylethylenediamine, N,N-di-tert-butylethylenediamine. N,N,N',N'-Tetramethylpropylenediamine, carbonamide, tetrahydropyrrole, imidazole, pyridine, piperidine, morpholine, potassium hydroxide and a combination thereof.

In summary, the biphenyl tetraphenol compound is prepared using an oxidative coupling method. The oxidative coupling method is divided into an acidic preparation and a basic preparation, which are performed through the following steps and parameters, respectively.

Acidic Preparation (201) A reaction solvent, an acid and a certain proportion of a metallic compound are added successively to a 5-20 L glass reactor, and uniformly stirred for 0.5-1 h at room temperature. A molar ratio of the metallic compound (acidic) to raw material (compound 1) is 0.1-1.5.

(202) A pre-dissolved raw material solution is slowly added dropwise into the reactor, and the reaction mixture is reacted under stirring at a temperature controlled by a high and low temperature circulation device for 1-12 h.

(203) After a large number of solid particles are precipitated, the reaction mixture is filtered to obtain anoxidative coupling product. If no solid particles are precipitated, the reaction mixture is subjected to rotary evaporation to obtain a viscous crude product. The viscous crude product is then pulped or recrystallized with at least one good solvent or poor solvent to precipitate the solid particles and filtered to obtain the oxidative coupling product. The two post-processing methods have similar yield (15%-75%).

Basic Preparation (301) A reaction solvent, an organic base and a certain proportion of a metallic complex are added successively to a 5-20 L glass reactor, and uniformly stirred at a rated temperature for 0.5-1 h. A molar ratio of the metallic complex (basic) to the organic base is (0.005-0.1):1, and a molar ratio of the catalyst to the raw material (compound 1) is (0.1-1.5):1.

(302) An air duct is inserted into the reaction mixture to continuously introduce oxygen or compressed air. The pre-dissolved raw material solution is slowly added dropwise into the reactor, and the reaction mixture is reacted under stirring at room temperature for 24-28 h, where the temperature is controlled by a high and low temperature circulation device.

(303) After the reaction is completed, the gas feeding is stopped. If a large number of solid particles are precipitated, the reaction mixture is filtered to obtain an oxidative coupling product. If there are no solid particles to be precipitated, the reaction mixture is subjected to rotary evaporation to obtain a viscous crude product. The viscous crude product is then pulped or recrystallized with at least one good solvent or poor solvent to precipitate the solid particles, and filtered to obtain the oxidative coupling product. The two post-processing methods have similar yield (55%-92%).

In an embodiment, the good solvent or the poor solvent is selected from the group consisting of water, methanol, tetrahydrofuran, acetonitrile, petroleum ether, n-hexane, n-heptane, diethyl ether, methyl tert-butyl ether, isopropyl ether, ethylene glycol, ethylene glycol dimethyl ether and a combination thereof. Preferably, the dual-solvent system used in the recrystallization is an ethyl acetate/petroleum ether system, a tetrahydrofuran/methanol system or a dichloromethane/n-hexane system (listed according to the polarity), and the single-solvent system is diethyl ether, acetonitrile, n-heptane and methanol.

In an embodiment, the biphenyl tetraphenol compound can be also prepared through the following steps.

(401) Resorcinol and sodium bicarbonate are ground, added with dimethyl sulfate and reacted under stirring at high temperature. Then the reaction mixture is washed and filtered to obtain 3-methoxyphenol.

(402) Toluene and an acid are added to the 3-methoxyphenol, and the reaction mixture is reacted at a high temperature to produce 2,4-di-tert-butyl-5-methoxy-phenol, where isobutylene is continuously introduced.

(403) The 2,4-di-tert-butyl-5-methoxy-phenol is added with methanol and a mixture of potassium ferricyanide and potassium hydroxide, and reacted at room temperature to obtain 3,3',5,5'-tetra-tert-butyl-6,6'-dimethoxy-2,2'-dihydroxy-1,1'-biphenyl.

(404) The 3,3',5,5'-tetra-tert-butyl-6,6'-dimethoxy-2,2'-dihydroxy-1,1'-biphenyl is added with dichloromethane under a nitrogen atmosphere, dropwise added with boron tribromide and reacted to obtain the biphenyl tetraphenol compound.

In an embodiment, the biphenyl tetraphenol compound can also be prepared through the following steps.

(501) Resorcinol is successively added with toluene and an acid, and reacted at a high temperature to obtain 4,6-di-tert-butyl-1,3-dihydroxy benzene, where isobutylene is continuously introduced.

(502) The 4,6-di-tert-butyl-1,3-dihydroxy benzene is dissolved in dichloromethane, to which a hydroxyl protecting agent and N,N-diisopropylethylamine are added successively. The reaction mixture is reacted at room temperature to obtain 2,4-di-tert-butyl-5-methoxy methyl ether-phenol.

(503) The 2,4-di-tert-butyl-5-methoxy methyl ether-phenol is added with methanol, dropwise added with a mixture of potassium ferricyanide and potassium hydroxide and reacted at room temperature to obtain 3,3',5,5'-tetra-tert-butyl-6,6'-dimethoxy-2,2'-dihydroxy-1,1'-biphenyl.

(504) The 3,3',5,5'-tetra-tert-butyl-6,6'-dimethoxy-2,2'-dihydroxy-1,1'-biphenyl is dissolved in isopropanol, to which concentrated hydrochloric acid is added dropwise.

The reaction mixture is reacted under stirring to obtain the biphenyl tetraphenol compound.

In an embodiment, the hydroxyl protecting agent is selected from the group consisting of 2-chlorotetrahydro-2H-pyran, 2-chloro-2-methylpropane, allyl chloride, benzyl chloride, tert-butyldiphenylchlorosilane, acetyl chloride, trimethylacetyl chloride, benzoyl chloride, tert-butyldimethylsilyl chloride and a combination thereof.

In an embodiment, the biphenyl tetraphenol compound can be also prepared through the following steps.

(601) m-Dimethoxybenzene is sequentially added with tetrahydrofuran and tetramethylethylenediamine, and then added with n-butyl lithium and ferric chloride under an argon atmosphere and a low temperature. The reaction mixture is heated to room temperature and reacted to obtain 2,2',6,6'-tetramethoxy-1,1'-biphenyl.

(602) The 2,2',6,6'-tetramethoxy-1,1'-biphenyl is added with dichloromethane, dropwise added with boron tribromide at a low temperature and then reacted under heating to obtain 2,2',6,6'-tetrahydroxy-1,1'-biphenyl.

(603) The 2,2',6,6'-tetrahydroxy-1,1'-biphenyl is added with tetrahydrofuran and an acid in nitrogen atmosphere, and reacted to obtain the biphenyl tetraphenol compound, where isobutylene is continuously introduced.

The acid is selected from the group consisting of formic acid, acetic acid, oxalic acid, dichloroacetic acid, trifluoroacetic acid, propionic acid, malonic acid, pyruvic acid, butyric acid, valeric acid, caproic acid, adipic acid, benzoic acid, p-nitrobenzoic acid, terephthalic acid, benzenesulfonic acid, fluorosulfonic acid, methanesulfonic acid, trifluoromethanesulfonic acid, p-toluenesulfonic acid, hydrobromic acid, hydrochloric acid, hydrofluoric acid, sulfurous acid, sulfuric acid, perchloric acid, phosphonic acid, pyrophosphoric acid, nitric acid, nitrous acid, chromic acid, fluoroantimony sulfonic acid, fluoroantimonic acid and a combination thereof.

The present disclosure further provides an application of the biphenyl tetradentate phosphite compound, including the following steps.

S701. The biphenyl tetradentate phosphite compound of claim 1 and a rhodium catalyst successively are added to a reactor device in an inert gas, where a molar ratio of the biphenyl tetradentate phosphite compound to the rhodium catalyst is (1-5):1. The biphenyl tetradentate phosphite compound is subjected to complexation in an organic solvent at room temperature under stirring.

S702: A mixed butene, a etherified butene, an olefin is added to the reactor under inert gas, such that a concentration of the rhodium catalyst is controlled at 50-200 ppm. The reaction mixture is subjected to a reaction at room temperature under stirring.

S703: Hydrogen and carbon monoxide are introduced into the reactor, where a pressure ratio of the hydrogen to the carbon monoxide is 1:(1-5) and a total pressure is 0.5-1 MPa. The reaction mixture is reacted at 40-80° C. under stirring for 1-4 h.

In an embodiment, the olefin is propylene (99 wt %), a mixed butene (consisting of 25 wt % of 1-butylene, 40 wt % of cis-2-butene and 35 wt % trans-2-butene) or a post-MTEB butene (consisting of 52.1 wt % of iso-butene, 16.6 wt % of 1-butylene, 15.3 wt % of cis-2-butene and 16.0 wt % of trans-2-butene). The purities of the cis-2-butene, trans-2-butene, 1,3-butadiene and etc are all above 98.0 wt %. The purities of the $C_5$-$C_{10}$ olefins are all above 95 wt %.

In an embodiment, the organic solvent is selected from the group consisting of toluene, dichloromethane, dichloroethane, hexane, ethyl acetate, dioxane, tetrahydrofuran and n-valeraldehyde.

The present disclosure will be further described in detail with reference to the embodiments. The compound used in individual embodiments is identical to the raw material shown in the corresponding synthesis route. For example, the compound 1 in the Example 9 is identical to the compound 1 in the corresponding synthetic route. In addition, it should be noted that these embodiments are merely illustrative of the disclosure, and are not intended to limit the disclosure. Improvements and adjustments made by those skilled in the art without departing from the spirit of the disclosure should fall within the scope of the disclosure.

Example 1 Preparation of Biphenyl Tetraphenol Compound in an Acidic System 4.5 mol of 4,6-di-tert-butylresorcinol and 3.8 L of an acidic solution were added to a 10 L double-layer jacketed glass reactor placed in a kilogram-level synthesis room with ventilation function, where the double-layer jacketed glass reactor was equipped with an explosion-proof mechanical agitator, a dropping funnel, an explosion-proof high and low temperature circulation device, a temperature probe, a reflux condenser and a discharge valve. After the 4,6-di-tert-butylresorcinol was completely dissolved, a solution of a metallic oxidant (0.5-5 mol) in 2 L of water was dropwise added, where due to the occurrence of a local heat release, it was required to operate the explosion-proof high and low temperature circulation to control the temperature of the reactor. After the addition was completed, the reaction mixture was reacted at −20-50° C. under stirring for 1-12 h. After the reaction was completed, if a large number of solid particles were precipitated in the reactor, the reaction mixture was batchwise filtered by a Buchner funnel or a centrifuge to obtain an oxidative coupling product, that was, 2,2',6,6'-tetrahydroxy-3,3',5,5'-tetra-tert-butyl-1,1'-biphenyl of formula 2. If there were no solid particles to be precipitated, the reaction mixture was subjected to rotary evaporation by an explosion-proof rotary evaporator to obtain a viscous crude product. The viscous crude product was added with pure water or a mixed solution of methanol and water in a ratio of (1-10):1 and beaten by a mechanical agitator until the solid particles were observed. The reaction mixture was filtered to obtain the oxidative coupling product. The two post-processing methods had similar yield (15%-75%).

Example 2 Preparation of Biphenyl Tetraphenol Compound in an Acidic Active Manganese Dioxide System 4.5 mol of 4,6-di-tert-butylresorcinol, 3.0 L of a mixture of acetic acid and water and 0.8 L of hexafluorophosphoric acid were added to a 10 L double-layer jacketed glass reactor placed in a kilogram-level synthesis room with ventilation function, where the double-layer jacketed glass reactor was equipped with an explosion-proof mechanical agitator, a dropping funnel, an explosion-proof high and low temperature circulation device, a temperature probe, a reflux condenser and a discharge valve. After the 4,6-di-tert-butylresorcinol was completely dissolved, a clear solution of 0.5 mol of active manganese dioxide and 2 L of water was dropwise added, where due to the occurrence of a local heat release, it was required to operate the explosion-proof high and low temperature circulation to control the temperature of the reactor. After the addition was completed, the reaction mixture was reacted at −20° C. under stirring for 6 h. After the reaction was completed, if a large number of solid particles were precipitated in the reactor, the reaction mixture was batchwise filtered by a Buchner funnel or a centrifuge to obtain an oxidative coupling product, that was, 2,2',6,6'-tetrahydroxy-3,3',5,5'-tetra-tert-butyl-1,1'-biphenyl of formula 2. If there were no solid particles to be precipitated, the reaction mixture was subjected to rotary evaporation by an explosion-proof rotary evaporator to obtain a viscous crude product. The viscous crude product was added with pure water or a mixed solution of methanol and water in a ratio of 1:2 and pulped with a mechanical agitator until solid particles emerged. The reaction mixture was filtered to obtain the oxidative coupling product. The two post-processing methods had similar yield (72%).

Example 3 Preparation of Biphenyl Tetraphenol Compound in an Acidic Ferric Chloride System 4.5 mol of 4,6-di-tert-butylresorcinol, 3.0 L of a mixture of acetic acid and tetrahydrofuran and 0.8 L of nitric acid were added to a 10 L double-layer jacketed glass reactor placed in a kilogram-level synthesis room with ventilation function, where the double-layer jacketed glass reactor was equipped with an explosion-proof mechanical agitator, a dropping funnel, an explosion-proof high and low temperature circulation device, a temperature probe, a reflux condenser and a discharge valve. After the 4,6-di-tert-butylresorcinol was completely dissolved, 5 mol of ferric chloride was quickly added to the double-layer glass jacketed reactor at −20° C., where due to the occurrence of a local heat release, it was required to operate the explosion-proof high and low temperature circulation to control the temperature of the reactor to keep it at 0° C. After the addition was completed, the reaction mixture was reacted at 0° C. under stirring for 10 h. After the reaction was completed, the reaction mixture was quickly filtered through a silica column with a negative pressure suction pump, thereby removing ferric chloride in the reaction mixture to obtain filtrate. The filtrate was subjected to rotary evaporation by an explosion-proof rotary evaporator to obtain a viscous crude product. A mixed solution of methanol and water in a ratio of 1:2 and pulped with a mechanical agitator until the solid particles were observed. The reaction mixture was filtered to obtain 2,2',6,6'-tetrahydroxy-3,3',5,5'-tetra-tert-butyl-1,1'-biphenyl of formula 2, which has a yield of 44%.

Table 1 Yields of the biphenyl tetraphenol compound under different reaction conditions

TABLE 1

Yields of the biphenyl tetraphenol compound under different reaction conditions

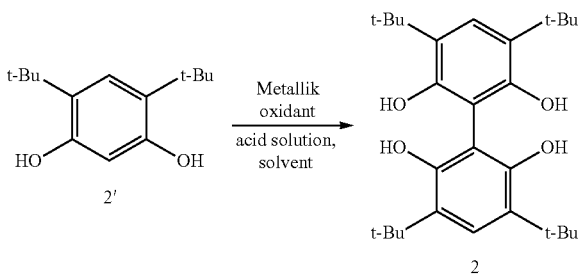 [SMILES: CC(C)(C)c1cc(C(C)(C)C)c(O)cc1O ; CC(C)(C)c1cc(C(C)(C)C)c(O)c(-c2c(O)c(C(C)(C)C)cc(C(C)(C)C)c2O)c1O]

| Serial number | Oxidant | Equivalent of oxidant [mol] | Acid | Solvent | Reaction temperature [° C.] | Time [hr] | Yield [%] |
|---|---|---|---|---|---|---|---|
| 1 | $K_7Cr_2O_7$ | 3.0 | $H_2SO_4$ | $AcOH/H_2O$ | 40 | 6 | 15 |
| 2 | $CrO_3$ | 3.0 | $H_2SO_4$ | $AcOH/H_2O$ | 40 | 6 | 24 |
| 3 | $KMnO_4$ | 0.5 | $HPF_6$ | $AcOH/H_2O$ | −20 | 2 | 32 |
| 4 | $MnO_2$ | 0.5 | $HPF_6$ | $AcOH/H_2O$ | −20 | 2 | 72 |
| 5 | $NaIO_3$ | 1.5 | HCl | $Ac_2O/H_2O$ | 30 | 10 | 48 |
| 6 | $NaClO_2$ | 1.5 | HCl | $Ac_2O/H_2O$ | 30 | 10 | 53 |
| 7 | $KClO_4$ | 1.5 | HCl | $Ac_2O/H_2O$ | 30 | 10 | 26 |
| 8 | $KHSO_5$ | 4.5 | HCl | $Ac_2O/H_2O$ | 30 | 10 | 38 |
| 9 | $FeCl_3$ | 5.0 | $HNO_3$ | $CHCOOH/H_2O$ | 50 | 12 | 44 |
| 10 | $CoF_3$ | 4.0 | $HNO_3$ | $HOOCCOOH/H_2O$ | 50 | 12 | 22 |

Example 4 Preparation of Biphenyl Tetraphenol Compound in an Alkaline Basic System 3 L of a reaction solvent, 0.0225-0.9 mol of a basic compound and 0.0225-0.45 mol of a metallic compound were added to a 10 L double-layer jacketed glass reactor in a kilogram-level synthesis room with ventilation function, where the double-layer jacketed glass reactor was equipped with an explosion-proof mechanical agitator, a dropping funnel, an explosion-proof high and low temperature circulation device, a temperature probe, a gas conduit, a reflux condenser and a discharge valve, and a molar ratio of the basic compound to the metallic compound was (1-10):1. The reaction mixture was evenly stirred at room temperature for 0.5-1 h to enable the complete dissolution, where during the stirring, oxygen or compressed air was continuously introduced below the surface of the reaction mixture. After a metal-organic base complex was formed, a 4,6-di-tert-butyl-resorcinol solution (4.5 mol, 3.8 L) was slowly added dropwise to the reactor with the dropping funnel, and the oxygen or gas was continuously introduced. After the addition was completed, the reaction mixture was reacted at 20-40° C. under stirring for 24-48 h. During the preparation process, the solvent was properly added to compensate for the solvent loss caused by the gas drainage. After the reaction was completed, if a large number of solid particles were precipitated in the reactor, the reaction mixture was batchwise filtered by a Buchner funnel or a centrifuge to obtain an oxidative coupling product, that was, 2,2',6,6'-tetrahydroxy-3,3',5,5'-tetra-tert-butyl-1,1'-biphenyl of formula 2. If there were no solid particles to be precipitated, the reaction mixture was subjected to rotary evaporation by an explosion-proof rotary evaporator to obtain a viscous crude product.

The viscous crude product was added with pure water or a mixed solution of methanol and water in a ratio of (1-10):1 and pulped with a mechanical agitator until solid particles emerged. The reaction mixture was filtered to obtain the oxidative coupling product. The two post-processing methods had similar yield (55%-92%).

Example 5 Preparation of Biphenyl Tetraphenol Compound in a Basic CuCl/Tetramethylethylenediamine (TMEDA) System 3 L of methanol, 0.05 mol of tetramethylethylenediamine and 0.0225 mol of cuprous chloride were added to a 10 L double-layer jacketed glass reactor placed in a kilogram-level synthesis room with ventilation function, where the double-layer jacketed glass reactor was equipped with an explosion-proof mechanical agitator, a dropping funnel, an explosion-proof high and low temperature circulation device, a temperature probe, a reflux condenser and a discharge valve. The reaction mixture was evenly stirred at room temperature for 1 h to enable the complete dissolution, where during the stirring, oxygen or compressed air was continuously introduced below the surface of the reaction mixture. After a metal-organic base complex was formed, a 4,6-di-tert-butylresorcinol solution (4.5 mol, 3.8 L) was slowly added dropwise to the reactor with the dropping funnel, and the oxygen or gas was continuously introduced. After the addition was completed, the mixture was maintained at 35° C. under stirring for 48 h. During the preparation process, the solvent was properly added to compensate for the solvent loss caused by the gas drainage. After the reaction was completed, if a large number of solid particles were precipitated in the reactor, the reaction mixture was batchwise filtered by a Buchner funnel or a centrifuge to obtain an oxidative coupling product, that was, 2,2',6,6'-tetrahydroxy-3,3',5,5'-tetra-tert-butyl-1,1'-biphenyl of formula 2. If there were no solid particles to be precipitated, the reaction mixture was subjected to rotary evaporation by an explosion-proof rotary evaporator to obtain a viscous crude product. The viscous crude product was added with pure water or a mixed solution of water and methanol in a ratio of 1:2 and pulped with a mechanical agitator until solid particles emerged. The reaction mixture was filtered to obtain the oxidative coupling product. The two post-processing methods had similar yield (around 70%).

Example 6 Preparation of Biphenyl Tetraphenol Compound in a Basic $K_3[Fe(CN)_6]$ System 3 L of a saturated aqueous solution of potassium hydroxide and 0.45 mol of potassium ferricyanide were added to a 10 L double-layer jacketed glass reactor in a kilogram-level synthesis room with ventilation function, where the double-layer jacketed glass reactor was equipped with an explosion-proof mechanical agitator, a dropping funnel, an explosion-proof high and low temperature circulation device, a temperature probe, a gas conduit, a reflux condenser and a discharge valve. The reaction mixture was evenly stirred at room temperature for 1 h to enable the complete dissolution, where during the stirring, oxygen or compressed air was continuously introduced below the surface of the reaction mixture. After a metal-organic base complex was formed, a 4,6-di-tert-butylresorcinol solution (4.5 mol, 3.8 L) was slowly added dropwise to the reactor with the dropping funnel, and the oxygen or gas was continuously introduced. After the addition was completed, the reaction mixture was maintained at 40° C. under stirring for 48 h. During the preparation process, the solvent was properly added to compensate for the solvent loss caused by the gas drainage. After the reaction was completed, if a large number of solid particles were precipitated in the reactor, the reaction mixture was batchwise filtered by a Buchner funnel or a centrifuge to obtain an oxidative coupling product, that was, 2,2',6,6'-tetrahydroxy-3,3',5,5'-tetra-tert-butyl-1,1'-biphenyl of formula 2. If there were no solid particles to be precipitated, the reaction mixture was subjected to rotary evaporation by an explosion-proof rotary evaporator to obtain a viscous crude product. The viscous crude product was added with a mixed solution of water and methanol in a ratio of 1:2 and pulped with a mechanical agitator until solid particles emerged. The reaction mixture was filtered to obtain the oxidative coupling product. The two post-processing methods had similar yield (around 55%)

TABLE 2

Yields of biphenyl tetraphenol compound under different reaction conditions

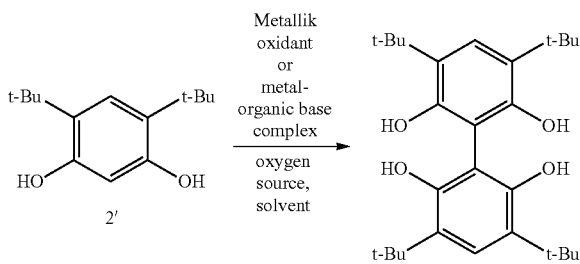

| No | Metallic compound | Equivalent of metal [mol] | Basic compound | Solvent | Oxygen source | Reaction temperature [° C.] | Time [hr] | Yield [%] |
|---|---|---|---|---|---|---|---|---|
| 1 | CuCl | 0.0225 | TMEDA | MeOH | $O_2$ | 25 | 24 | 70 |
| 2 | CuCl | 0.0225 | $Et_3N$ | EtOH | $O_2$ | 25 | 24 | 68 |

TABLE 2-continued

Yields of biphenyl tetraphenol compound under different reaction conditions

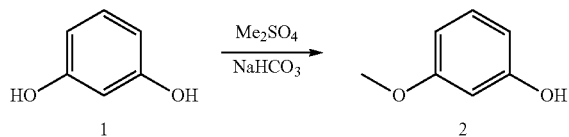

| No | Metallic compound | Equivalent of metal [mol] | Basic compound | Solvent | Oxygen source source | Reaction temperature [° C.] | Time [hr] | Yield [%] |
|---|---|---|---|---|---|---|---|---|
| 3 | CuCl$_2$ | 0.05 | TMEDA | MeOH | O$_2$ | 25 | 24 | 84 |
| 4 | CuCl$_2$ | 0.05 | DTEDA | iPrOH | Air | 35 | 24 | 73 |
| 5 | Cu(OTf)$_2$ | 0.15 | TMPDA | Acetone | H$_2$O$_2$ | 25 | 36 | 66 |
| 6 | CuI | 0.20 | DMAEA | MeOH | Oxone | 25 | 24 | 90 |
| 7 | CuSO$_4$ | 0.25 | TEEDA | EtOAc | TBHP | 40 | 48 | 71 |
| 8 | [Cu(MeCN)$_4$][PF$_6$] | 0.30 | N/A | MeOH | O$_2$ | 25 | 24 | 92 |
| 9 | CuCl(OH)(TMEDA) | 0.10 | N/A | CH$_2$CL$_2$ | O$_2$ | 25 | 24 | 65 |
| 10 | CuBr(OH)(TMEDA) | 0.25 | N/A | CH$_2$CL$_2$ | O$_2$ | 25 | 24 | 67 |
| 11 | K$_3$[Fe(CN)$_6$] | 0.45 | N/A | KOH/H$_2$O | Air | 25 | 48 | 55 |
| 12 | Co(acae)$_2$ | 0.45 | TMEDA | iPrOH | O$_2$ | 35 | 24 | 56 |
| 13 | PDC | 0.30 | N/A | EtOH | Air | 40 | 24 | 62 |

Example 7 Preparation of 3-Methoxyphenol

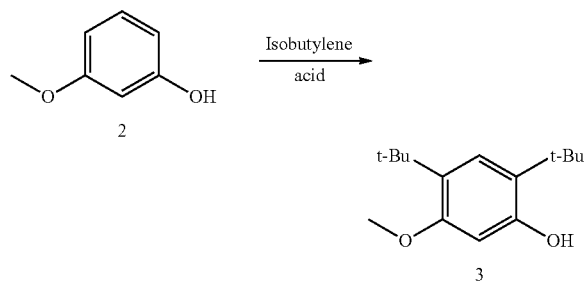

2.2 g of compound 1 and 10.0 g of sodium bicarbonate were ground into powders, 2.5 g of dimethyl sulfate was added, and the reaction mixture was reacted at 60° C. under vigorous stirring for 1 h. washed with 50 mL of water to remove the base and filtered to obtain a crude product. The crude product was subjected to recrystallization with ethyl acetate-n-hexane to produce 1.98 g of a pure product with a yield of 79%.

Example 8 Preparation of 2,4-di-tert-butyl-5-methoxyphenol 24.8 g of compound 2, 200 mL of methylbenzene and 5.16 g of p-toluenesulfonic acid (PTSA) were added successively to a 1 L three-necked flask. The reaction mixture was heated to 95° C. and reacted for 12 h, during which isobutylene gas was continuously introduced. After the reaction was completed, the reaction mixture was subjected to rotary evaporation, added with 100 mL of water and subjected to extraction three times with ethyl acetate each for 100 mL. The organic phases were combined, dried with anhydrous sodium sulfate, dried by rotary evaporation and then subjected to rapid column chromatography to obtain 10.0 g of the target product with a yield of 42%.

Example 9 Preparation of 4,6-di-tert-butyl-1,3-benzenediol

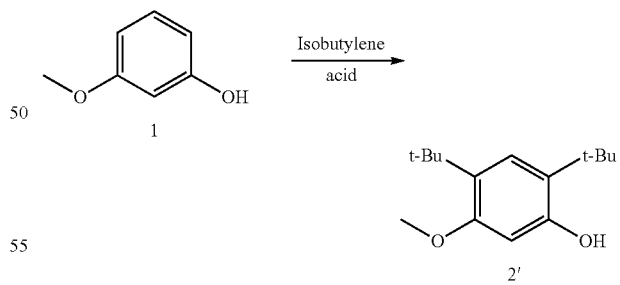

26.3 g of compound 1, 200 mL of methylbenzene and 5.16 g of PTSA were added successively to a 1 L three-necked flask. The reaction mixture was heated to 95° C. and reacted for 12 h, during which isobutylene gas was continuously introduced. After the reaction was completed, the reaction mixture was subjected to rotary evaporation, added with 100 mL of water and subjected to extraction three times with ethyl acetate each for 100 mL. The organic phases were combined, dried with anhydrous sodium sulfate, dried by rotary evaporation and then subjected to rapid column chromatography to obtain 15.0 g of the target product with a yield of 56%.

Example 10 Preparation of 2,4-di-tert-butyl-5-methoxy methyl ether-phenol

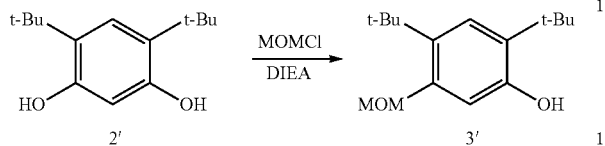

15.0 g of compound 2' was dissolved in 200 mL of dichloromethane in a 1 L three-necked flask, to which 5 mL of chloromethoxymethyl ether and 10 mL of diisopropylethylamine (DIEA) were added successively. The reaction mixture was reacted at room temperature for 12 h. After the reaction was completed, the reaction mixture was added with 250 mL of saturated ammonium chloride, dried by rotary evaporation, added with 100 mL of water and subjected to extraction three times with ethyl acetate each for 100 mL. The organic phases were combined, dried with anhydrous sodium sulfate, dried by rotary evaporation and then subjected to rapid column chromatography to obtain 13.7 g of a target product with a yield of 71%.

Example 11 Preparation of 3,3',5,5'-tetra-tert-butyl-6,6'-dimethoxy-2,2'-dihydroxy-1,1'-biphenyl

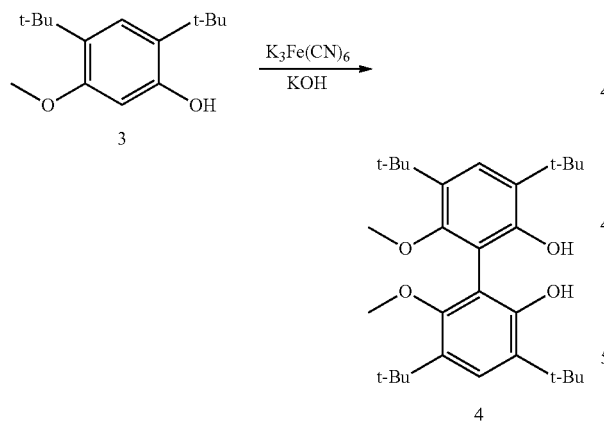

6.0 g of compound 3 and 100 mL of methanol were added successively to a 500 mL single-necked round-bottom flask. 8.37 g of potassium ferricyanide and 4.58 g of potassium hydroxide were dissolved in 100 mL of water to obtain a mixed solution, which was added dropwise to the round-bottom flask. The reaction mixture was reacted at room temperature for 2 h. After the reaction was completed, the reaction mixture was concentrated, added with 200 mL of water, and subjected to extraction three times with ethyl acetate each for 100 mL. The organic phases were combined, dried under vacuum, heated at 100° C. for 2 h and recrystallized with petroleum ether to obtain 2.9 g of a target product with a yield of 50%.

Example 12 Preparation of 3,3',5,5'-tetra-tert-butyl-6,6'-dimethoxy methyl etheryl-2,2'-dihydroxy-1,1'-biphenyl

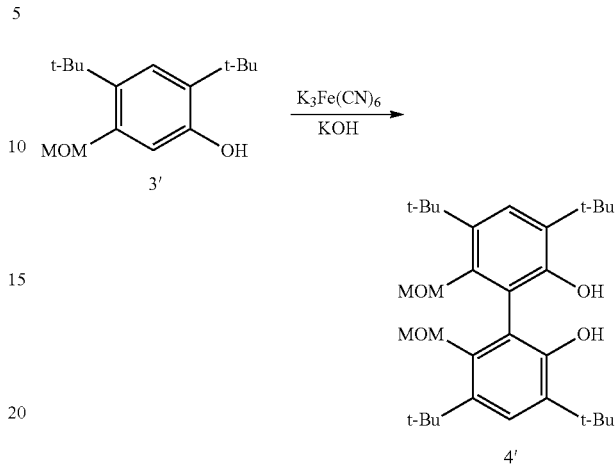

5.5 g of compound 3' and 100 mL of methanol were added successively to a 500 mL single-necked round-bottom flask. 9.12 g of potassium ferricyanide and 5.36 g of potassium hydroxide were dissolved in 100 mL of water to obtain a mixed solution, which was added dropwise to the round-bottom flask. The reaction mixture was reacted at room temperature for 2 h. After the reaction was completed, the reaction mixture was concentrated, added with 200 mL of water, and subjected to extraction three times with ethyl acetate each for 100 mL. The organic phases were combined, dried under vacuum, heated at 100° C. for 2 h and recrystallized with petroleum ether to obtain 2.6 g of a target product with a yield of 47%.

Example 13 Preparation of 3,3',5,5'-tetra-tert-butyl-2,2',6,6'-tetra-hydroxy-1,1'-biphenyl (Route 1)

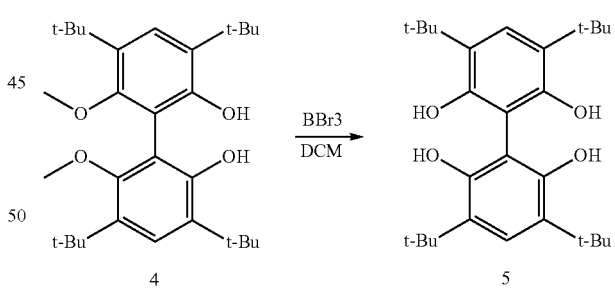

2.0 g of compound 4 was added to a 200 mL dry Schlenk flask, in which the gas was replaced with nitrogen. 50 mL of dichloromethane was added to the Schlenk flask at 25° C. 2.34 g of boron tribromide was added dropwise to the Schlenk flask, and the reaction mixture was reacted for 6 h. After that, the reaction was quenched with water, and the reaction mixture was added with 50 mL of water and subjected to extraction three times with ethyl acetate each for 100 mL. The organic phases were combined, dried with anhydrous sodium sulfate and subjected to rotary evaporation to obtain a white solid. The white solid was treated by rapid column chromatography to obtain 1.8 g of a target product with a yield of 96%.

Example 14 Preparation of 3,3',5,5'-tetra-tert-butyl-2,2',6,6'-tetra-hydroxy-1,1'-biphenyl (Route 2)

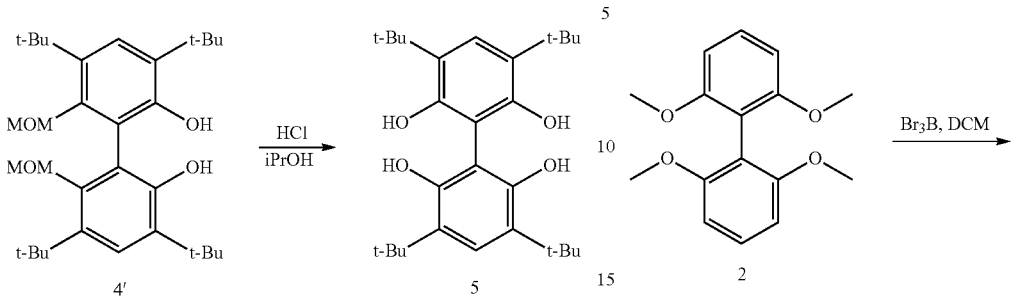

2.5 g of compound 4 was dissolved in 40 mL of isopropanol in a 200 mL round-bottom flask, to which 4 drops of concentrated hydrochloric acid was added. The reaction mixture was reacted at 55° C. under stirring for more than 10 h until the raw material was confirmed by thin layer chromatography (TLC) to be completely consumed. Then the reaction mixture was added with 25 mL of saturated sodium bicarbonate and subjected to extraction three times with ethyl acetate each for 50 mL. The organic phases were combined, dried with anhydrous sodium sulfate and subjected to rotary evaporation to obtain a white solid. The white solid was treated by rapid column chromatography to obtain 2.0 g of a target product with a yield of 98%.

Example 15 Preparation of 2,2',6,6'-tetramethoxy-1,1'-biphenyl

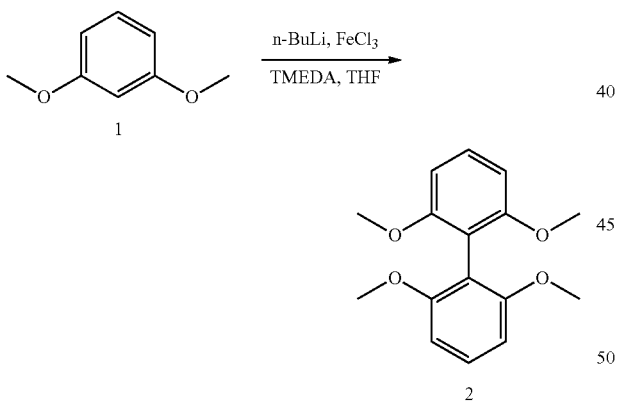

13.8 g of compound 1, 200 mL of tetrahydrofuran and 16 g of tetramethylethylenediamine were added successively to a 1 L three-necked flask which is in an argon atmosphere. 40 mL of 2.5 mol/L n-butyl lithium and 16.1 g of ferric chloride were added successively in the flask at −78° C. After the addition was completed, the flask was heated to room temperature to react for 24 h. After the reaction was completed, the reaction mixture was concentrated, and added with 400 mL of water, and subjected to extraction three times with ethyl acetate each for 500 mL. The organic phase was combined, dried with anhydrous sodium sulfate and subjected to rotary evaporation to obtain a residue. The residue was treated by rapid column chromatography to obtain 22 g of a target product with a yield of 80%.

Example 16 Preparation of 2,2',6,6'-tetrahydroxy-1,1'-biphenyl

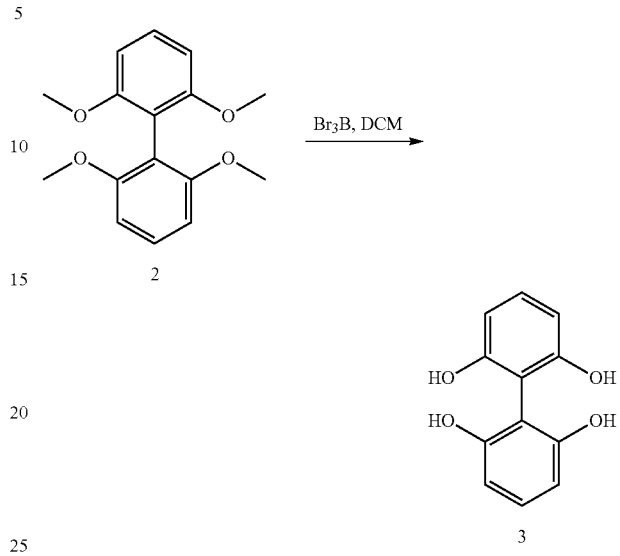

27 g of compound 2 and 500 mL of dichloromethane were added successively to a 1 L four-necked round-bottom flask. 101 g of boron tribromide was added dropwise in the flask at −30° C. After the addition was completed, the reaction mixture was heated to 30° C. and reacted for 4 h. After the reaction was completed, the reaction mixture was concentrated, and added with 400 mL of water, and subjected to extraction three times with ethyl acetate each for 600 mL to obtain a residue. The residue was treated by rapid column chromatography to obtain 20.5 g of a target product with a yield of 91%.

Example 17 Preparation of 2,2',6,6'-tetrahydroxy-3,3',5,5'-tetra-tert-butyl-1,1'-biphenyl

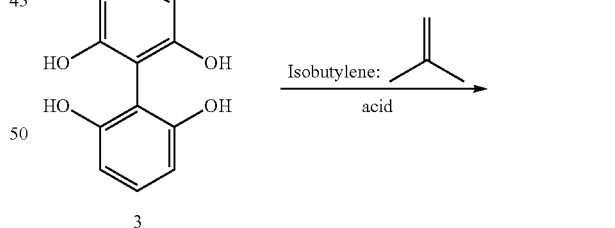

22.0 g of compound 3 was added in a 1 L dry Schlenk flask, in which the gas was replaced with nitrogen. 200 mL of tetrahydrofuran and 1.0 g of acetic acid were added to the Schlenk flask at 25° C. 1.5 atmospheric pressure of isobutylene was continuously introduced, and the reaction mixture was reacted for 12 h. After that, the reaction was quenched with water, the reaction mixture was added with 300 mL of water and subjected to extraction three times with ethyl acetate each for 400 mL. The organic phases were combined, dried with anhydrous sodium sulfate and subjected to rotary evaporation to obtain a faint yellow solid. The faint yellow solid was treated by rapid column chromatography to obtain 40.0 g of a target product with a yield of 90%.

$^1$H NMR (600 MHz, (CD$_3$)$_2$SO): δ=7.53 (s, 4H), 7.17 (s, 2H), 1.37 (s, 36H). A hydrogen-nuclear magnetic resonance ($^1$H NMR) spectrum of the 2,2',6,6'-tetramethoxy-3,3',5,5'-tetra-tert-butyl-1,1'-biphenyl was presented in FIG. 1.

Example 18 Preparation of 1,1'-biphenyl-2,2'-diyl phosphorochloridite

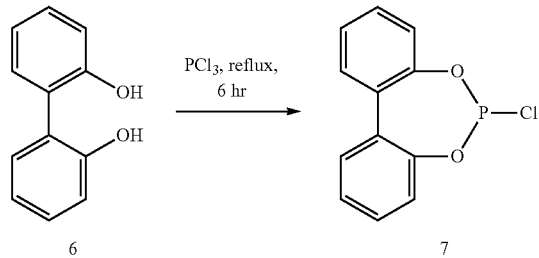 [SMILES: Oc1ccccc1-c1ccccc1O ; Clp1oc2ccccc2c2ccccc2o1]

20 g of 2,2'-biphenol was added to excess phosphorus trichloride, an the reaction mixture was heated under reflux for 6 h and distilled under vacuum to remove the excess phosphorus trichloride to obtain 18 g of a yellow oily product 7 with a yield of 71%.

Example 19 Preparation of 2,2',6,6'-tetra[(1,1-biphenyl-2,2'-diyl)phosphite]-3,3',5,5'-tetra-tert-butyl-1,1'-biphenyl (Route 1)

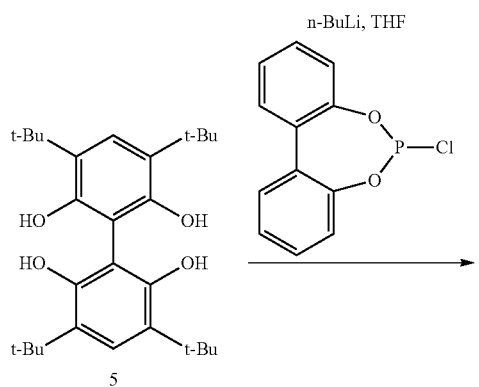

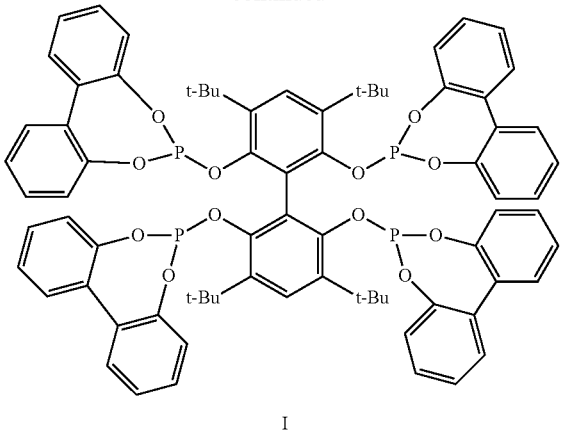

4.2 g of 2,2',6,6'-tetrahydroxy-3,3',5,5'-tetra-tert-butyl-1,1'-biphenyl and 100 mL anhydrous tetrahydrofuran were added successively to a 2 L Schlenk flask in the nitrogen atmosphere. 15 mL of 2.5 mol/L n-butyllithium were added dropwise to the flask at −78° C. After the addition was completed, the flask was heated to room temperature to react for 1 h. After the reaction was completed, the reaction mixture was added dropwise to 100 mL of anhydrous tetrahydrofuran solution of 13 g of 1,1'-biphenyl-2,2'-diyl phosphorochloridite at −78° C. After the addition was completed, the reaction mixture was subjected to react at room temperature for 24 h. Finally, reaction mixture was concentrated in the nitrogen atmosphere to obtain a residue. The residue was treated by rapid column chromatography to obtain 6.0 g of a target product with a yield of 46%.

$^1$H NMR (400 MHz, CDCl$_3$): δ=7.74 (s, 2H), 7.48-7.38 (m, 8H), 7.19 (td, J=7.6, 7.2, 2.2 Hz, 8H), 7.11 (dd, J=6.5, 1.7 Hz, 16H), 1.30 (s, 36H).
$^{31}$P NMR (243 MHz, CDCl$_3$): δ=140.62.
APCI-TOF/MS: Calculated for C$_{76}$H$_{71}$O$_{12}$P$_4$[M+H]$^+$: 1299.3818; Found: 1299.3891.

Figure 2:
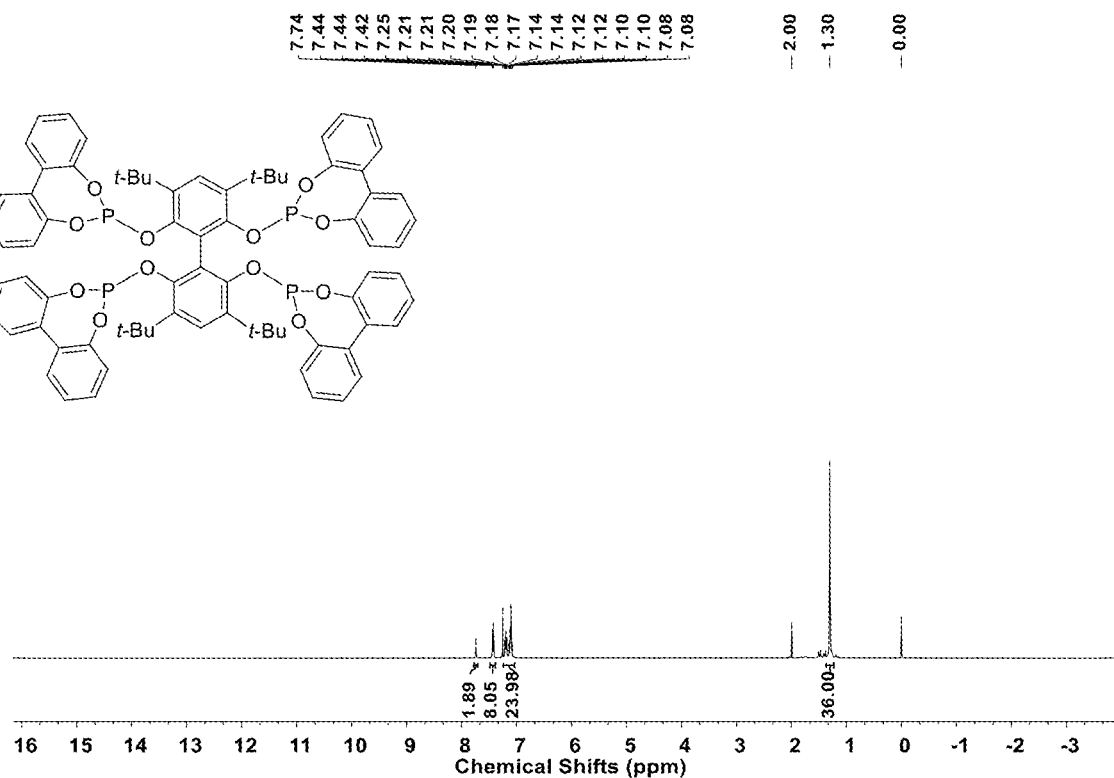
FIG. 2 is an $^1$H NMR spectrum of 2,2',6,6'-tetra[(1,1'-biphenyl-2,2'-diyl)phosphite]-3.3',5,5'-tetra-tert-butyl-1,1'-biphenyl according to an embodiment of the present disclosure.
Figure 3:
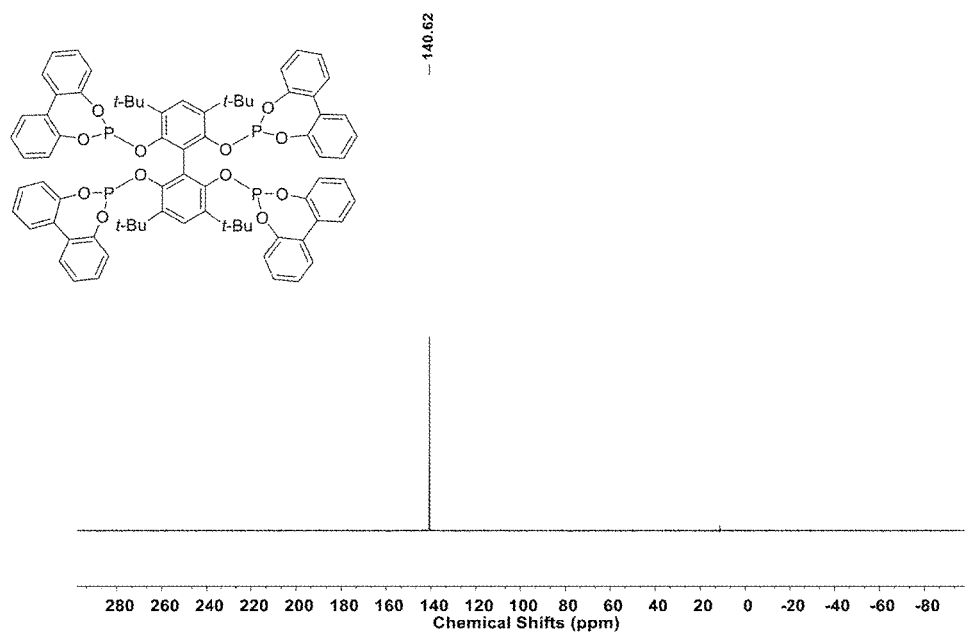
FIG. 3 is a phosphorus-nuclear magnetic resonance ($^{31}$P NMR) spectrum of the 2,2',6,6'-tetra[(1,1'-biphenyl-2,2'-diyl)phosphite]-3,3',5,5'-tetra-tert-butyl-1,1'-biphenyl according to an embodiment of the present disclosure.
Figure 4:
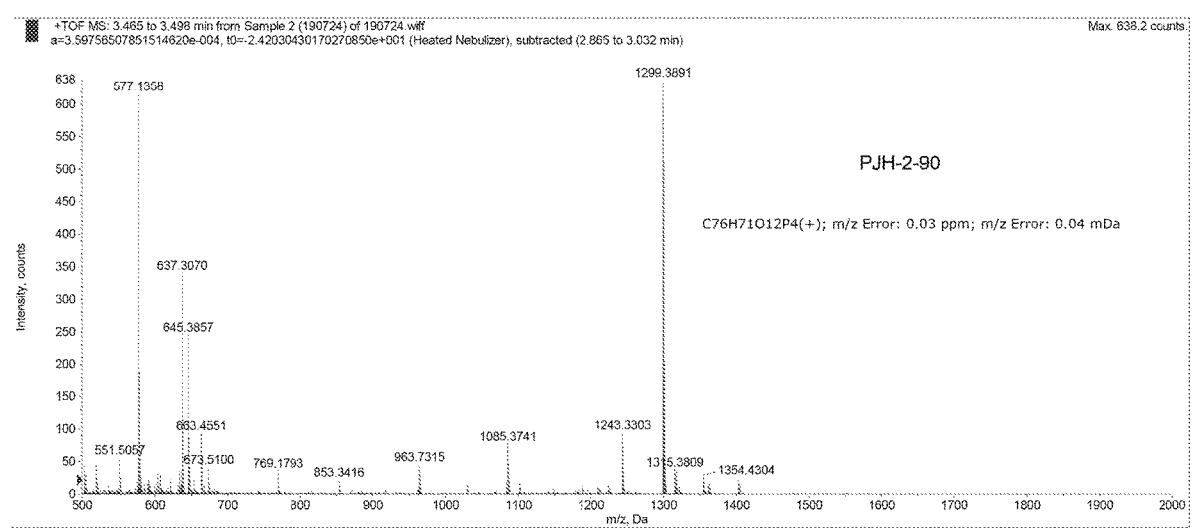
FIG. 4 is a high resolution mass spectrum of the 2,2',6,6'-tetra[(1,1'-biphenyl-2,2'-diyl)phosphite]-3,3',5,5'-tetra-tert-butyl-1,1'-biphenyl according to an embodiment of the present disclosure.
Figure 5:
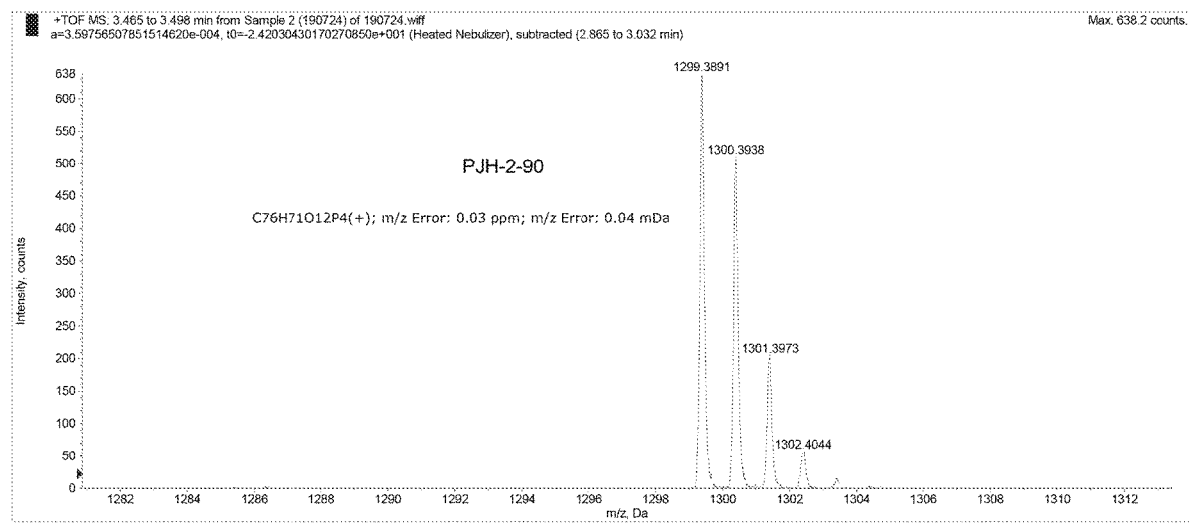
FIG. 5 is a partial enlarged view of the high resolution mass spectrum provided in FIG. 4.

$^1$H NMR spectrum of the 2,2',6,6'-tetra[(1,1'-biphenyl-2,2'-diyl)phosphite]-3,3',5,5-tetra-tert-butyl-1,1'-biphenyl (L1) was presented in FIG. 2. A phosphorus-nuclear magnetic resonance ($^{31}$P NMR) spectrum of the L1 was presented in FIG. 3. A high resolution mass (UPLC APCI-TOF-MS) spectrum of the L1 was presented in FIG. 4. A partial enlarged view of the UPLC APCI-TOF-MS spectrum provided in FIG. 4 was presented in FIG. 5.

Example 20

Rh(acac)(CO)$_2$ (2.6 mg, 0.01 mmol), 0.01 mmol of L, 4.6 mL of methylbenzene and 0.64 mL of internal standard n-decane were added to a 200 mL stainless steel high-pressure reactor under an argon atmosphere, where the high-pressure reactor was equipped with a pressure sensor, a temperature probe, an online sampling port and a pressure-relief valve. The reaction mixture was magnetically stirred for 10 min to synthesize a rhodium-ligand complex catalyst. Subsequently, a gas pipeline was connected, and the air in the reactor was fully replaced. Through switching a two-position four-way valve, 3.6 mL of liquefied trans-2-butene was added to the reactor by using a plunger pump with a metering function, and a concentration of the rhodium catalyst in the reaction mixture was controlled at about 159 ppm. The reaction mixture was stirred evenly at room temperature for 10 min. 3.5 bar of carbon monoxide and 3.5 bar of hydrogen were introduced into the reactor. A bottom and a body of the reactor were heated by a magnetic stirrer and an electric heating jacket, respectively, to raise the temperature to 65° C. The reaction mixture was reacted at a constant pressure of 1.0 MPa for 2 h and then cooled to room temperature by a −40° C. cooling jacket. The online sampling port was opened for sampling without opening the reactor. The sample was diluted with HPLC-grade ethyl acetate, and a molar ratio of n-valeraldehyde to 2-methylbutanal was determined by gas chromatography (GC) to be 15.6:1, where the n-valeraldehyde had a selectivity of 94.0%, and a conversion rate of the raw material was 90.1%.

Example 21

Rh(acac)(CO)$_2$ (2.6 mg, 0.01 mmol), 0.03 mmol of L1, 4.6 mL of methylbenzene and 0.64 mL of internal standard n-decane were added to a 200 mL stainless steel high-pressure reactor under an argon atmosphere, where the high-pressure reactor was equipped with a pressure sensor, a temperature probe, an online sampling port and a pressure-relief valve. The reaction mixture was magnetically stirred for 10 min to synthesize a rhodium-ligand complex. Subsequently, a gas pipeline was connected, and the air in the reactor was fully replaced. Through switching a two-position four-way valve, 3.6 mL of liquefied trans-2-butene was added in the reactor by using a plunger pump with a metering function, and a concentration of the rhodium catalyst in the reaction mixture was controlled at about 159 ppm. The reaction mixture was stirred evenly at room temperature for 10 min. 3.5 bar of carbon monoxide and 5 bar of hydrogen were introduced into the reactor. A bottom and a body of the reactor were heated by a magnetic stirrer and an electric heating jacket, respectively, to raise the temperature to 85° C. The reaction mixture was reacted at a constant pressure of 0.85 MPa for 1.5 h and then cooled to room temperature by a −40° C. cooling jacket. The online sampling port was opened for sampling without opening the reactor. The sample was diluted with HPLC-grade ethyl acetate, and a molar ratio of n-valeraldehyde to 2-methylbutanal was determined by GC to be 14:1, where the n-valeraldehyde has a selectivity of 93.5%, and a conversion rate of the raw material was 94.2%.

Example 22

Rh(acac)(CO)$_2$(2.6 mg, 0.01 mmol), 0.05 mmol of L1, 4.6 mL of methylbenzene and 0.64 mL of internal standard n-decane were added to a 200 mL stainless steel high-pressure reactor under an argon atmosphere, where the high-pressure reactor was equipped with a pressure sensor, a temperature probe, an online sampling port and a pressure-relief valve. The reaction mixture was magnetically stirred for 10 min to synthesize a rhodium-ligand complex. Subsequently, a gas pipeline was connected, and the air in the reactor was fully replaced. Through switching a two-position four-way valve, 3.6 mL of a mixed butene was added to the reactor by using a plunger pump with a metering function, where the mixed butene consisted of 1-butene, cis-2-butene and trans-2-butene in a molar ratio of 0.2:0.3:0.5. A concentration of the rhodium catalyst in the reaction mixture was controlled at about 159 ppm. The reaction mixture was stirred evenly at room temperature for 10 min. 5 bar of carbon monoxide and 5 bar of hydrogen were introduced into the reactor. A bottom and a body of the reactor were heated by a magnetic stirrer and an electric heating jacket, respectively, to raise the temperature to 70° C. The reaction mixture was reacted at a constant pressure of 1.0 MPa for 1.5 h and then cooled to room temperature by a −40° C. cooling jacket. The online sampling port was opened for sampling without opening the reactor. The sample was diluted with HPLC-grade ethyl acetate, and a molar ratio of n-valeraldehyde to 2-methylbutanal was determined by GC to be 25:1, where the n-valeraldehyde has a selectivity of 96.2%, and a conversion rate of the raw material was 89.7%.

Other phosphorochloridites (L2-L26) of the disclosure can be prepared using a phosphine chloride derivative of a corresponding aryl substituent according to the process mentioned in Example 16.

In conclusion, compared to the bidentate phosphite ligand (Biphephos), the biphenyl tetradentate phosphite compound provided herein has simple synthesis, high yield, high yield of linear aldehyde products, good reaction activity and excellent stability to water and oxygen. In addition, the biphenyl tetradentate phosphite compound is suitable for the large-scale production. At the same time, it has been experimentally demonstrated that compared to the Biphephos and other bidentate phosphorous ligands, the biphenyl tetradentate phosphite ligand proposed herein can achieve higher conversion rate and n-product/iso-product ratio, and better activity and stability when employed in the hydroformylation with the mixed butene or the post-etherified butene. As a consequence, the biphenyl tetradentate phosphite ligand has a promising industrial application prospect.

The above-mentioned embodiments are only illustrative of this application, and are not intended to limit the scope of this application. It should be noted that various modifications and improvements made by those of ordinary skill in the art without departing from the concept of this application should fall within the scope of this application defined by the appended claims.

Described above are only preferred embodiments of this application, and are not intended to limit this application. Any modification, replacement and improvement made without departing from the spirit of this application shall fall within the scope of this application.

What is claimed is:

1. A biphenyl tetradentate phosphite compound of formula(I):

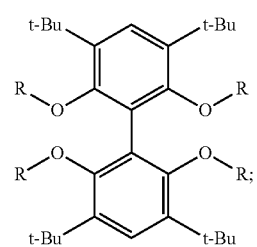

wherein R is selected from the group consisting of:

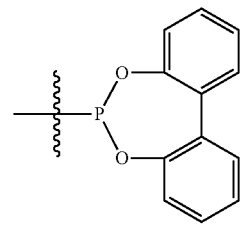

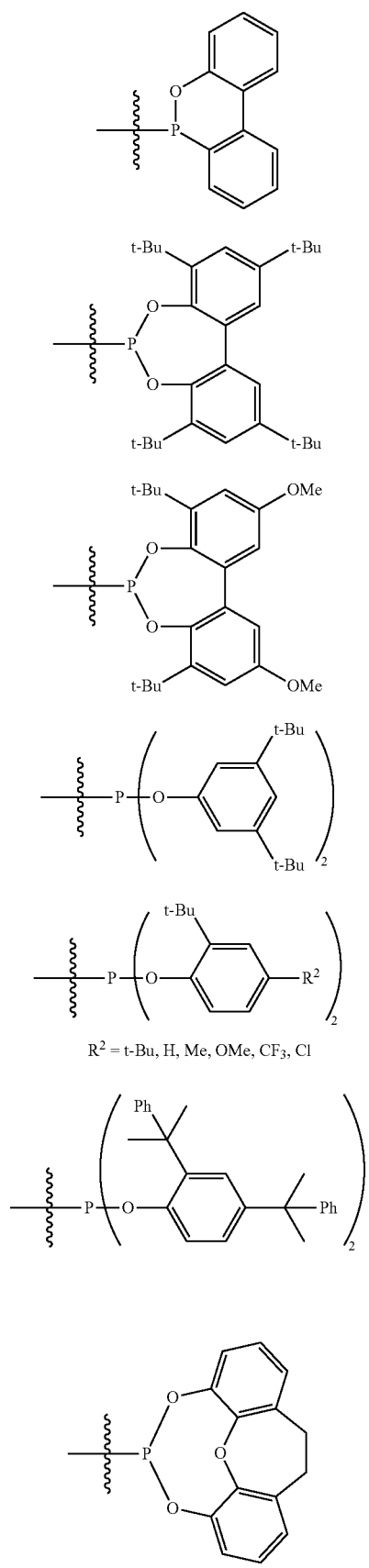
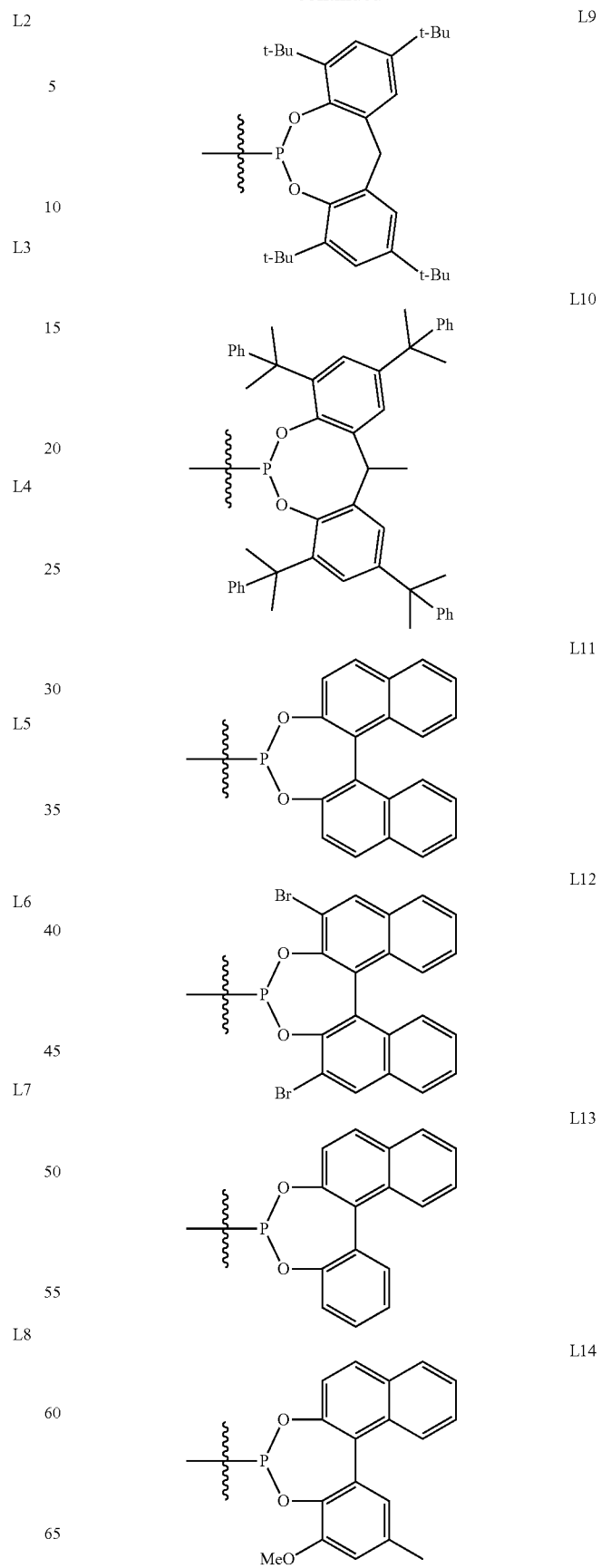

-continued

L15

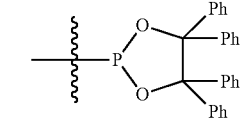

L16

L17

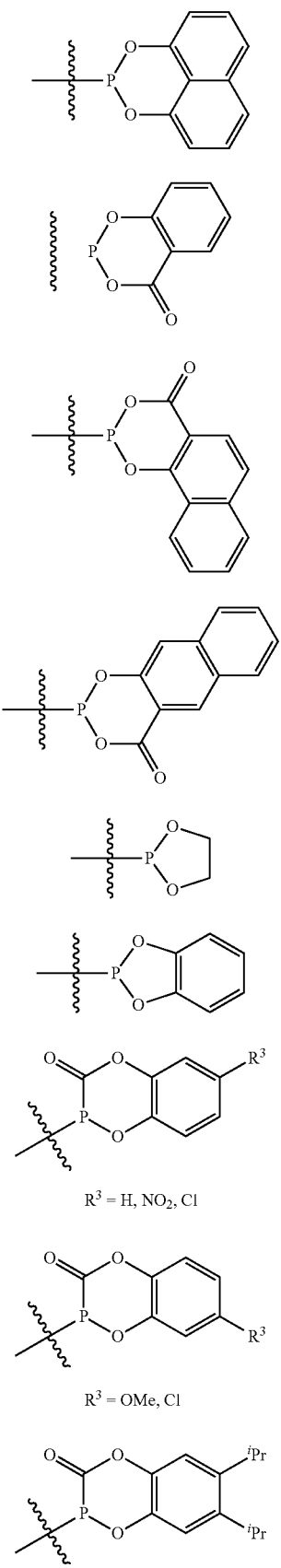

L18

L19

L20

L21

L22

L23

-continued

L25

L26 and hydrogen.

2. A method of preparing the biphenyl tetradentate phosphite compound of claim 1, comprising:
reacting a biphenyl tetraphenol compound with phosphorochloridite in an organic solvent in the presence of n-butyl lithium to produce the biphenyl tetradentate phosphite compound;
wherein the phosphorochloridite is selected from L1-L26.

3. The method of claim 2, the step of "reacting a biphenyl tetraphenol compound with phosphorochloridite" comprises:
adding the biphenyl tetraphenol compound and the organic solvent to a reactor successively under a nitrogen atmosphere; dropwise adding the n-butyl lithium at a low temperature; and heating the reaction mixture to room temperature followed by reaction under reflux; and
dropwise adding a phosphorochloridite solution of the biphenyl, methylene dibenzyl, binaphthyl, benzoyloxy, ortho-phenyl, phenyl, naphthyl or aryl group at low temperature; and reacting the reaction mixture at room temperature followed by concentration to obtain the biphenyl tetradentate phosphite compound.

4. The method of claim 3, wherein the biphenyl tetraphenol compound is prepared by a reaction of 4,6-di(tert-butyl)benzene-1,3-diol under the action of a metallic oxidant, an acid and a reaction solvent.

5. The method of claim 3, wherein the biphenyl tetraphenol compound is prepared through steps of:
dissolving 4,6-di(tert-butyl)benzene-1,3-diol in an acid in a reacting kettle; dropwise adding a metallic oxidant and a reaction solvent; and reacting the reaction mixture at −20-50° C. for 1-12 h followed by filtration to obtain the biphenyl tetraphenol compound; wherein a molar ratio of the metallic oxidant to the 4,6-di(tert-butyl)benzene-1,3-diol is (0.1-1.5):1.

6. The method of claim 4, wherein the acid is selected from the group consisting of concentrated sulfuric acid, concentrated hydrochloric acid, concentrated nitric acid, phosphonic acid, hexafluorophosphoric acid, hypochlorous acid, chlorous acid, formic acid, glacial acetic acid, peroxyacetic acid, 3-chloroperoxybenzoic acid, acetic anhydride, propionic acid, butyric acid, valeric acid, caproic acid, octanoic acid, capric acid, adipic acid, oxalic acid, malonic acid, succinic acid and a combination thereof.

7. The method of claim 4, wherein the metallic oxidant is selected from the group consisting of cuprous chloride, copper chloride, cuprous iodide, copper iodide, cuprous bromide, cupric bromide, copper sulfate, cupric nitrate, copper trifluoromethanesulfonate, ferrous chloride, ferric trichloride, nickel oxide, nickel dioxide, manganese trioxide, active manganese dioxide, potassium permanganate, cobalt(III) fluoride, cobaltic oxide, chromium trioxide, chromium dioxide, chromium(III) oxide, chromic acid, potassium dichromate, sodium dichromate, magnesium oxide, sodium iodate, sodium periodate, sodium hypochlorite, sodium chlorite, sodium chlorate, sodium perchlorate, potassium iodate, potassium periodate, potassium hypochlorite, potassium chlorite, potassium chlorate, potassium perchlorate, potassium persulfate, potassium hydrogen persulfate and a combination thereof.

8. The method of claim 3, wherein the biphenyl tetraphenol compound is prepared by a reaction of 4,6-di(tert-butyl) benzene-1,3-diol under the action of a metal complex, a basic compound, an oxygen source and a reaction solvent.

9. The method of claim 3, wherein the biphenyl tetraphenol compound is prepared through steps of:
adding a reaction solvent, an basic compound and a metal complex sequentially to a reacting kettle: reacting the reaction mixture at room temperature under stirring in the presence of an oxygen source to prepare a metal-organic base complex; dropwise adding 4,6-di(tert-butyl)benzene-1,3-diol to the reacting kettle, wherein the oxygen source is continuously introduced; and reacting the reaction mixture at −20-50° C. for 24-28 h followed by filtration to obtain the biphenyl tetraphenol compound, wherein a molar ratio of the metal complex to the 4,6-di(tert-butyl)benzene-1,3-diol is (0.005-0.1): 1.

10. The method of claim 4, wherein the reaction solvent is selected from a group consisting of water, methanol, ethanol, isopropanol, n-butanol, tert-butanol, dichloromethane, dichloroethane, trichloromethane, benzene, toluene, xylene, 1,2-dichlorobenzene, ethyl acetate, dioxane, tetrahydrofuran, acetone, glacial acetic acid, N-methylpyrrolidone, N,N-dimethylformamide, N,N-dimethylacetamide and a combination thereof.

11. The method of claim 5, wherein the reaction solvent is selected from a group consisting of water, methanol, ethanol, isopropanol, n-butanol, tert-butanol, dichloromethane, dichloroethane, trichloromethane, benzene, toluene, xylene, 1,2-dichlorobenzene, ethyl acetate, dioxane, tetrahydrofuran, acetone, glacial acetic acid, N-methylpyrrolidone, N,N-dimethylformamide, N,N-dimethylacetamide and a combination thereof.

12. The method of claim 8, wherein the oxygen source is selected from the group consisting of oxygen, air, ozone, diacetoxyiodobenzene, hydrogen peroxide, tert-butyl hydroperoxide, dibenzoyl peroxide, cyclohexanone peroxide, p-benzoquinone, dichlorodicyanobenzoquinone and a combination thereof.

13. The method of claim 8, wherein the metal complex is selected from the group consisting of CuOAc, $Cu(OAc)_2$, $Cu(OTf)_2$, $[Cu(NH_3)_4]SO_4$, $[Cu(NH_3)_4](OH)_2$, CuCl(OH) TMEDA, $Cu(TMEDA)Cl$, $Cu(TMEDA)Cl_2$, $Cu(Et_3N)Cl_2$, $Cu(DTEDA)Cl_2$, $Cu(morpholine)_2Cl_2$, $Cu(PDA)_2Cl_2$, $Cu_2(TEEDA)_2Br_2$, $[Cu(MeCN)_4][PF_6]$, $Cu(PPh_3)_2Cl_2$, $K_3[Fe(CN)_6]$, $K_4[Fe(CN)_6]$, $K_3[Fe(NCS)_6]$, $Na_3[Fe(CN)]$, $Na_4[Fe(CN)_6]$, $Na_3[Fe(NCS)_6]$, $Fe(PPh_3)Cl$, $Ni(acac)_2$, $Ni(OAc)_2$, $Ni(CO)_4$, $Mn(acac)_2$, $Mn(OAc)_2$, $Co(acac)_2$, $Co(acac)_3$, $[Co(NH_3)_3]Cl$, $[Co(NH_3)_6]Cl_3$, $[Co(NO_2)_3(NH_3)_3]$, $Co(OAc)_2$, $CrCl_3.6H_2O$, $[Cr(H_2O)_6]Cl_3$, $[CrCl(H_2O)_5]Cl_2$, $[CrCl_2(H_2O)_4]Cl$, $[CrCl_2(H_2O)_4]Cl.2H_2O$, pyridinium chlorochromate, pyridinium dichromate, $[Mg(ClO_4)_2].6H_2O$ and a combination thereof.

14. The method of claim 8, wherein the basic compound is selected from the group consisting of methylamine, ethylamine, dimethylamine, diethylamine, trimethylamine, triethylamine, N,N'-dimethylaniline, N-methylaniline, aniline, diphenylamine, ethylenediamine, N-methylethylenediamine, N,N-dimethylethylenediamine, N,N'-dimethylethylenediamine, N,N,N'-trimethylethylenediamine, N,N,N',N'-tetramethylethylenediamine, N-ethylethylenediamine, N,N'-diethylethylenediamine, N,N-diethylethylenediamine, N,N,N'-triethylethylenediamine, N,N,N',N'-tetradiethylethylenediamine, N,N-di-tert-butylethylenediamine, N,N,N',N'-Tetramethylpropylenediamine, carbonamide, tetrahydropyrrole, imidazole, pyridine, piperidine, morpholine, potassium hydroxide and a combination thereof.

15. The method of claim 3, wherein the biphenyl tetraphenol compound is prepared through steps of:
grinding resorcinol and sodium bicarbonate into powders followed by adding dimethyl sulfate; and reacting the reaction mixture under stirring at high temperature followed by washing and filtration to obtain 3-methoxyphenol;
adding toluene and an acid to the 3-methoxyphenol, and reacting the reaction mixture at a high temperature to produce 2,4-di-tert-butyl-5-methoxyphenol, wherein isobutylene is continuously introduced;
adding methanol and a mixture of potassium ferricyanide and potassium hydroxide to the 2,4-di-tert-butyl-5-methoxy-phenol; reacting the reaction mixture at room temperature to obtain 3,3',5,5'-tetra-tert-butyl-6,6'-dimethoxy-2,2'-dihydroxy-1,1'-biphenyl; and
adding dichloromethane to the 3,3',5,5'-tetra-tert-butyl-6,6'-dimethoxy-2,2'-dihydroxy-1,1'-biphenyl under nitrogen atmosphere; and dropwise adding boron tribromide for a reaction to obtain the biphenyl tetraphenol compound.

16. The method of claim 3, wherein the biphenyl tetraphenol compound is prepared through steps of:
adding toluene and an acid to resorcinol followed by a high-temperature reaction to obtain 4,6-di-tert-butyl-1,3-dihydroxy benzene, wherein isobutylene is continuously introduced;
dissolving the 4,6-di-tert-butyl-1,3-dihydroxy benzene in dichloromethane; adding successively a hydroxyl protecting agent and N,N-diisopropylethylamine; and reacting the reaction mixture at room temperature to obtain 2,4-di-tert-butyl-5-methoxy methyl ether-phenol;
adding methanol to the 2,4-di-tert-butyl-5-methoxy methyl ether-phenol, and dropwise adding a mixture of potassium ferricyanide and potassium hydroxide; reacting the reaction mixture at room temperature to obtain 3,3',5,5'-tetra-tert-butyl-6,6'-dimethoxy-2,2'-dihydroxy-1,1'-biphenyl; and
dissolving the 3,3',5,5'-tetra-tert-butyl-6,6'-dimethoxy-2,2'-dihydroxy-1,1'-biphenyl in isopropanol; dropwise adding concentrated hydrochloric acid; and reacting the reaction mixture under stirring to obtain the biphenyl tetraphenol compound.

17. The method of claim 3, wherein the biphenyl tetraphenol compound is prepared through steps of:
sequentially adding tetrahydrofuran and tetramethylethylenediamine tom-dimethoxybenzene; adding n-butyl lithium and ferric chloride under an argon atmosphere and a low temperature; and reacting the reaction mixture at room temperature to obtain 2,2',6,6'-tetramethoxy-1,1'-biphenyl;
adding dichloromethane to the 2,2',6,6'-tetramethoxy-1,1'-biphenyl; adding dropwise boron tribromide at the low temperature: reacting the reaction mixture under heating to obtain 2,2',6,6'-tetrahydroxy-1,1'-biphenyl; and adding tetrahydrofuran and an acid to the 2,2',6,6'-tetrahydroxy-1,1'-biphenyl in nitrogen atmosphere for a reaction to obtain the biphenyl tetraphenol compound, wherein isobutylene is continuously introduced.

18. The method of claim 15, wherein the acid is selected from the group consisting of formic acid, acetic acid, oxalic acid, dichloroacetic acid, trifluoroacetic acid, propionic acid, malonic acid, pyruvic acid, butyric acid, valeric acid, caproic acid, adipic acid, benzoic acid, p-nitrobenzoic acid, terephthalic acid, benzenesulfonic acid, fluorosulfonic acid, methanesulfonic acid, trifluoromethanesulfonic acid, p-toluene sulfonic acid, hydrobromic acid, hydrochloric acid, hydrofluoric acid, sulfurous acid, sulfuric acid, perchloric acid, phosphonic acid, pyrophosphoric acid, nitric acid, nitrous acid, chromic acid, fluoroantimony sulfonic acid, fluoroantimonic acid and a combination thereof.

19. The method of claim 16, wherein the hydroxyl protecting agent is selected from the group consisting of 2-chlorotetrahydro-2H-pyran, 2-chloro-2-methylpropane, allyl chloride, benzyl chloride, tert-butyldiphenylchlorosilane, acetyl chloride, trimethylacetyl chloride, benzoyl chloride, tert-butyldimethylsilyl chloride and a combination thereof.

20. An application of the biphenyl tetradentate phosphite compound of claim 1 in the hydroformylation reaction of a $C_2$-$C_{10}$ olefin, comprising:

adding the biphenyl tetradentate phosphite compound and a rhodium catalyst successively to a reactor in an inert gas, wherein a molar ratio of the biphenyl tetradentate phosphate compound to the rhodium catalyst is (1-5):1; and subjecting the biphenyl tetradentate phosphite compound to complexation in an organic solvent at room temperature under stirring;

adding a mixed butene, a etherified butene, cis-2-butene or trans-2-butene to the reactor under inert gas such that a concentration of the rhodium catalyst is controlled at 50-200 ppm; and subjecting the reaction mixture to a reaction at room temperature under stirring; and introducing hydrogen and carbon monoxide into the reactor, wherein a pressure or volume ratio of the hydrogen to the carbon monoxide is (1-1.5):1 or 1:(1-1.5) and a total pressure is 0.5-1.5 MPa; and reacting the reaction mixture at 40-80° C. under stirring for 1-4 h.

* * * * *